United States Patent [19]

Ono et al.

[11] Patent Number: 5,589,510
[45] Date of Patent: Dec. 31, 1996

[54] METHOD FOR INHIBITING RETROVIRAL INFECTION BY ADMINISTERING A NAPHTHALENESULFONIC ACID COMPOUND

[75] Inventors: Mitsunori Ono; Yumiko Wada, both of Lexington; Yaming Wu, Cambridge, all of Mass.; Hiroshi Kitaguchi, Kanagawa, Japan; Yumiko Jimbo, Asaka, Japan; Ryoichi Nemori, Kanagawa, Japan; Stephen Gillies, Hingham; Kin-Ming Lo, Wellsley, both of Mass.

[73] Assignee: Fuji Immunopharmaceuticals Corp., Lexington, Mass.

[21] Appl. No.: 441,219

[22] Filed: May 15, 1995

Related U.S. Application Data

[63] Continuation-in-part of Ser. No. 253,156, Jun. 2, 1994, abandoned.

[51] Int. Cl.⁶ .......................... A61K 31/175; A61K 31/16; A61K 31/10

[52] U.S. Cl. .................... 514/590; 514/613; 514/614; 514/708; 514/934

[58] Field of Search ............................ 514/590, 613, 514/614, 708, 934

[56] References Cited

PUBLICATIONS

Ciba Ltd., Chem. Abs. 59:8916b.
Dreyfuss, Chem. Abs. 64:2907b.
Mohan, P., et al., J. Med. Chem., 36, pp. 1996–2003.
Dreyfuss et al., Chem. Abs. 56:557i 1962.
Dreyfuss et al., Chem. Abs. 56:7469c 1962.
Dreyfuss, Chem. Abs. 56:7469f 1962.
Ciba Ltd., Chem. Abs. 58:8074a 1963.

*Primary Examiner*—Raymond Henley, III
*Attorney, Agent, or Firm*—Sughrue, Mion, Zinn, Macpeak & Seas

[57] ABSTRACT

A method for inhibiting retroviral infection in a subject comprising administering to said subject a therapeutically effective amount of a naphthalenesulfonic acid compound or a pharmaceutically acceptable salt thereof, as herein defined.

14 Claims, No Drawings

METHOD FOR INHIBITING RETROVIRAL INFECTION BY ADMINISTERING A NAPHTHALENESULFONIC ACID COMPOUND

The subject application is a Continuation-In-Part of U.S. application Ser. No. 08/253,156, filed on Jun. 2, 1994, now abandoned, which is incorporated in its entirety.

FIELD OF THE INVENTION

The present invention relates to a method for inhibiting retroviral infection in a subject comprising administering to the subject a therapeutically effective amount of a naphthalenesulfonic acid compound or pharmaceutically acceptable salt thereof as herein defined.

BACKGROUND OF THE INVENTION

Acquired human immunodeficiency syndrome (hereinafter "AIDS") has been characterized by a depletion of $CD4^+$ lymphocytes. As a consequence, T-cell mediated immunity is impaired in AIDS patients, resulting in the occurrence of severe opportunistic infections and unusual neoplasms.

AIDS results from the infection of T lymphocytes and other immune cells with a collection of closely related retroviruses (LAV, HTLV-III, HIV or ARV). The range of infectivity of these agents is generally restricted to cells expressing the CD4 glycoprotein on their surface. Thus, the CD4 glycoprotein is believed to serve not only as a receptor for molecules on the surface of target cells, but also as a receptor for retroviral infection.

A variety of compounds have been shown to be able to block the binding of retroviruses, such as HIV, to its cellular receptor, CD4. CD4 is the general terminology for the human CD4 receptor and its counterparts in other mammalian cells. These compounds include soluble human CD4 (Smith et al., Science, 238:1704–1707 (1987)); and synthetic fragments of human CD4 (Lifson et al., Science, 241:712–716 (1988)). Other known anti-retroviral compounds include dextran sulfate (Ito et al., Antivir. Res., 7:361–367 (1987)).

In addition, the following compounds having sulfo moieties have been reported to be effective inhibitors of several significant steps in the HIV replication cycle:

(a) Evans Blue (EB) has been reported to be an inhibitor of the interaction of HIV rgp120 with CD4 cells (Balzarini et al., Biochem. Biophys. Res. Commun., 136:64–71 (1986));

(b) Suramin and Direct Yellow 50 have been reported to be inhibitors of reverse transcriptase (Balzarini et al., Int. J. Cancer, 37:451 (1986)); and (c) bis-Naphthalenedisulfonic acid (Mohan et al., Life Science, 47:993 (1990); and Tan et al., J. Med. Chem., 35:4846 (1992)), and Fuchsin Acid (Baba et al., Biochem. Biophys. Res. Commun., 155:1404 (1988)) have been reported to be inhibitors of syncytium formation.

However, most of the anti-retroviral compounds that have been heretofore described in the art cannot be administered for a prolonged period of time because of their toxicity (see U.S. Pat. No. 5,153,181). In addition, they do not have sufficient efficacy because of their weak retroviral inhibitory activity.

All U.S. patents and publications referred to herein are hereby incorporated by reference.

SUMMARY OF THE INVENTION

Accordingly, an object of the present invention is to provide compounds with low toxicity and high retroviral inhibitory activity for use in a method of inhibiting retroviral infection.

An additional object of the present invention is to provide compounds that inhibit the interaction of retroviral glycoproteins which often involve fusion of virion with host cell.

Still another object of the present invention is to provide compounds useful in a method of inhibiting reverse transcriptase.

These and other objects of the present invention, which will be apparent from the detailed description of the present invention provided hereinafter, have been met by a method for inhibiting retroviral infection in a subject comprising administering to said subject a therapeutically effective amount of a naphthalenesulfonic acid compound represented by formula (I) or a pharmaceutically acceptable salt thereof:

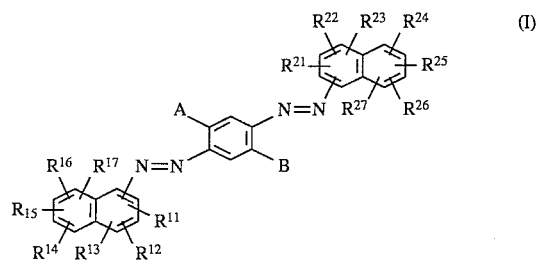

wherein $R^{11}$ to $R^{27}$ are individually selected from the group consisting of hydrogen atom, hydroxyl group, amino group which is optionally substituted with alkly or aryl groups, sulfo groups, carboxyl groups, amide group which is optionally substituted with alkly or aryl groups, acylamino groups, sulfonamide groups, sulfonylamino groups, alkoxy groups and halogen atoms;

provided that at least one of $R^{11}$ to $R^{17}$ is hydroxyl or amino group, at least one of $R^{21}$ to $R^{27}$ is hydroxyl or amino group, at least one of $R^{11}$ to $R^{17}$ is sulfo group, and at least one of $R^{21}$ to $R^{27}$ is sulfo group;

A and B are individually selected from the group consisting of hydrogen atom, alkyl $(C_1-C_4)$ groups, alkoxy $(C_1-C_4)$ groups, and halogen atoms.

Suitable examples of alkyl or aryl substituted amino groups include amino groups substituted by alkyl having 1 to 12 carbon atoms or aryl having 6 to 12 carbon atoms, such as methylamino, butylamino, dimethylamino and phenylamino (anilino) groups.

Suitable examples of alkyl or aryl substituted amide groups include amide groups substituted by alkyl having 1 to 12 carbon atoms or aryl having 6 to 12 carbon atoms, such as $—CONHCH_3$, $—CONHC_4H_9$, $—CONHC_8H_{17}$ and $—CONHPh$.

Suitable examples of acylamino groups are represented by the formula $R^1—(Y)_n—CONH—$ wherein $R^1$ is selected from the group consisting of substituted or unsubstituted alkyl $(C_1-C_{12})$, substituted or unsubstituted aryl $(C_6-C_{12})$, and substituted or unsubstituted heteroaryl $(C_1-C_{12})$ group, Y represents $—NH—$, $—CH_2—$, or $—OCH_2—$; and n is 0 or 1.

Suitable examples of sulfonylamino groups are represented by the formula $R^1—(Y)_n—SO_2NH—$ wherein $R^1$, Y and n are the same as defined above.

Suitable examples of alkoxy groups include those having 1 to 6 carbon atoms, such as methoxy, ethoxy, butoxy and hexyloxy.

Suitable examples of halogen atoms include fluorine, chlorine, bromine and iodine.

According to one of the preferred embodiments of the present invention, there is provided a method for inhibiting retroviral infection in a subject comprising administering to said subject a therapeutically effective amount of a naphthalenesulfonic acid compound represented by formula (II) or a pharmaceutically acceptable salt thereof:

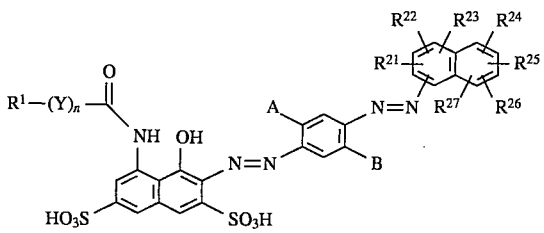

wherein $R^{21}$ to $R^{27}$ are individually selected from the group consisting of hydrogen atom, hydroxyl group, amino group which is optionally substituted with alkly or aryl groups, sulfo groups, carboxyl groups, amide group which is optionally substituted with alkly or aryl groups, acylamino groups, sulfonamide groups, sulfonylamino groups, alkoxy groups and halogen atoms;

provided that at least one of $R^{21}$ to $R^{27}$ is hydroxyl or amino group, and at least one of $R^{21}$ to $R^{27}$ is sulfo group;

A and B are individually selected from the group consisting of hydrogen atom, alkyl ($C_1$–$C_4$) groups, alkoxy ($C_1$–$C_4$) groups, and halogen atoms;

$R^1$ is selected from the group consisting of substituted or unsubstituted alkyl ($C_1$–$C_{12}$) substituted or unsubstituted aryl ($C_6$–$C_{12}$), and substituted or unsubstituted heteroaryl ($C_1$–$C_{12}$) group, Y represents —NH—, —$CH_2$—, or —$OCH_2$—; and n is 0 or 1.

According to another preferred embodiment of the present invention, there is provided a method for inhibiting retroviral infection in a subject comprising administering to said subject a therapeutically effective amount of a naphthalenesulfonic acid compound represented by formula (III) or a pharmaceutically acceptable salt thereof:

naphthalenesulfonic acid compound represented by formula (I), (II) or (III) or a pharmaceutically acceptable salt thereof.

Suitable examples of alkyl having 1 to 12 carbon atoms for $R^1$, $R^2$ and $R^3$ include a straight chain or branched, substituted or unsubstituted alkyl having from 1 to 12 carbon atoms (e.g., $CH_3$, $C_2H_5$, n-$C_4H_9$, n-$C_6H_{13}$, t-$C_5H_{11}$, $CH_2C_6H_5$, etc.), and a substituted or unsubstituted cycloalkyl having 3 to 6 carbon atoms (e.g., cyclopropyl, cyclopentyl, or cyclohexyl).

Suitable examples of aryl having 6 to 12 carbon atoms for $R^1$, $R^2$ and $R^3$ include a substituted or unsubstituted phenyl, substituted or unsubstituted α- and β-naphthyl. Suitable examples of substituents of substituted phenyl or naphthyl include halogen atoms, trifluoromethyl, alkyl, alkoxy, alkylcarbonyl, aryl, aryloxy, arylcarbonyl, cyano and hydroxyl groups. Among them, preferred are halogen atoms such as fluorine or chlorine, trifluoromethyl, alkyl having 1 to 4 carbon atoms and alkoxy having 1 to 4 carbon atoms. Most preferred are halogen atoms, in particular, chlorine atom.

If $R^1$, $R^2$ or $R_3$ is a chlorine substituted phenyl group, the number of the chlorine atoms substituted on the phenyl group is preferably 1 to 3, more preferably 1 or 2. If $R^1$, $R^2$ or $R^3$ is a mono-chloro substituted phenyl group, the substituted position may be o-, m- or p-. If $R^1$, $R^2$ or $R^3$ is a di-chloro substituted phenyl group, examples of such groups include 2,4-dichlorophenyl, 3,4-dichlorophenyl, 2,3-dichlorophenyl and 2,5-dichlorophenyl groups.

Suitable examples of heteroaryl having 1 to 12 carbon atoms for $R^1$, $R^2$ and $R^3$ include pyridyl, thienyl, furyl, quinolyl and isoquinolyl groups. Suitable examples of substituents on the heteroaryl groups include halogen atoms such as fluorine, chlorine, bromine and iodine, trifluoromethyl, alkyl, alkoxy, aryl, cyano and hydroxyl groups. Among them, preferred are halogen atoms such as fluorine or chlorine and alkyl having 1 to 4 carbon atoms. Suitable examples of substituted or unsubstituted heteroaryl groups include 3-pyridyl, 4-pyridyl, 2-thienyl, 2-furyl, and 3-quinolyl. Particularly preferred are 3-pyridyl and 3-quinolyl.

In the formulas (I) to (IV), A and B may be the same or different and represent individually hydrogen atom, alkyl

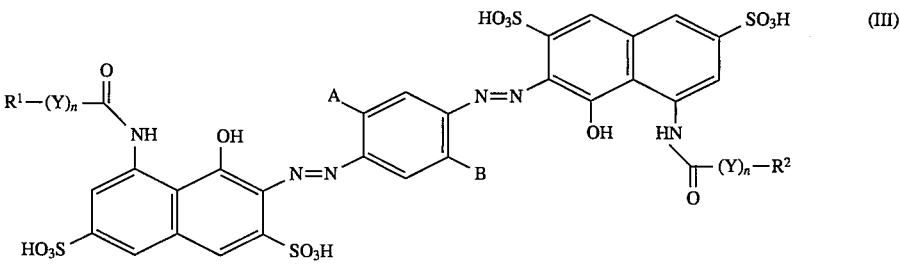

wherein $R^1$ and $R^2$ are individually selected from the group consisting of substituted or unsubstituted alkyl ($C_1$–$C_{12}$), substituted or unsubstituted aryl ($C_6$–$C_{12}$), and substituted or unsubstituted heteroaryl ($C_1$–$C_{12}$) group;

A and B are individually selected from the group consisting of hydrogen atom, alkyl ($C_1$–$C_4$) group, alkoxy ($C_1$–$C_4$) group, and halogen atom; Y represents —NH—, —$CH_2$—, or —$OCH_2$—; and n is 0 or 1.

DETAILED DESCRIPTION OF THE INVENTION

As discussed above, an object of the present invention has been met by use of a therapeutically effective amount of a having 1 to 4 carbon atoms, alkoxy having 1 to 4 carbon atoms and halogen atoms. Suitable examples of alkyl groups include methyl, ethyl, and butyl groups. Suitable examples of alkoxy groups include methoxy, ethoxy and butoxy groups. Suitable examples of halogen atoms include fluorine, chlorine and bromine atoms. Alkyl and alkoxy groups are preferred and alkoxy group is particularly preferred.

A and B may be the same or different but preferably the same. More preferably, A and B are alkoxy groups having 1 to 4 carbon atoms and most preferably A and B are methoxy groups.

As used herein, the term "pharmaceutically acceptable salt" means a salt having the biological activity of the parent compound, but lacking any unusual toxic activity at the selected administration level. Examples of such salts include inorganic sodium, potassium and ammonium salts; organic amine salts such as diethanolamine, triethanolamine, and cyclohexylamine salts; amino acid salts such as tyrosine and lysine salts; amides such as tyrosinamide; and tris(hydroxyethyl)amine. Preferred examples of pharmaceutically acceptable salts of the compounds of this invention which can be employed include Na, K, tyrosinamide and lysine salts.

The naphthalenesulfonic acid compounds employed in the method of the present invention generally have the ability to inhibit the fusion of virions to target cells (peripheral blood lymphocytes), and to inhibit reverse transcriptase. Thus, the compounds of the present invention can be used for the treatment and/or prophylaxis of human and animal diseases, particularly mammalian diseases, caused by HIV and other retroviruses, such as HIV-1, SIV, CHJ and HSD.

The compounds used in the method of the present invention can be administered to the subject, e.g., to a human, other mammals or other animals, in a manner which inhibits or prevents viral infection or replication.

More specifically, the compounds can be formulated into a pharmaceutical composition comprising a therapeutically effective amount of the compound and a pharmaceutically acceptable carrier. The therapeutically effective amount of the compound and the specific pharmaceutically acceptable carrier will vary depending upon, e.g., the age, weight, sex of the subject, the mode of administration, and the type of viral condition being treated.

In a particular aspect, the pharmaceutical composition which can be used to inhibit retroviral infections comprises the compounds of the present invention in effective unit dosage form. As used herein, the term "effective unit dosage" or "effective unit dose" is used herein to mean a predetermined anti-retroviral amount sufficient to be effective against the viral organisms in vivo.

The pharmaceutical compositions may contain the compound used in the method of this invention in an amount of from 0.01 to 99% by weight of the total composition, preferably 0.1 to 80% by weight of the total composition. For oral administration, the compound is generally administered in an amount of 0.1 g/body to 15 g/body, preferably 0.5 g/body to 5 g/body. For intravenous injection, the dose may be about 0.1 to about 30 mg/kg/day, preferably about 0.5 to about 10 mg/kg/day. If applied topically as a liquid, ointment, or cream, the compound may be present in an amount of about 0.1 to about 50 mg/ml, preferably about 0.5 to 30 mg/ml of the composition.

When the compounds according to the invention are formulated for injection, the dose may be presented in unit dose form in ampoules or in multi-dose containers with added pharmaceutically acceptable adjuvants such as a preservative.

In addition, the compositions may take forms such as suspensions, solutions, or emulsions in oily or aqueous vehicles, and may contain formulating agents, such as suspending, stabilizing, or dispersing agents, isotonic agents and/or dissolving co-solvents conventionally cited in the pharmaceutical art.

Alternatively, the compounds used in the present invention may be employed in powder form for constitution with a suitable vehicle, e.g., sterile, pyrogen-free water, before use.

Further, for infections of external tissues, e.g., the mouth and skin, the compositions may be applied to the infected part of the body of the subject or the susceptible parts of the body to be infected as a topical ointment, cream or gargle.

The compounds may also be applied into body orifices, such as the rectum and vagina, in the form of a suppository or cream.

The compounds used in the present invention may be presented in an ointment or cream, for instance with a water soluble ointment base, in a concentration of from about 0.1 to 100% (w/v), preferably 0.5 to 90% (w/v).

In the cases of inhalations or aerosol preparations, the compounds employed in the invention, in the form of a liquid or a minutely ground powder, may be filled in an aerosol container with gas or liquid spraying agents, and if desired, together with conventional adjuvants, such as humidifying agents.

The compounds used in the present invention may also be formulated as pharmaceuticals for non-pressured preparations, such as in a nebulizer or an atomizer, or in the form of a controlled release formulation or a biodegradable implant.

For systemic administration, the daily dosage as employed for adult human treatment will range from about 0.1 mg/kg to about 150 mg/kg, preferably about 0.2 mg/kg to about 80 mg/kg.

For topical administration, the daily dosage as employed for adult human treatment will range from about 0.01 mg/kg to about 50 mg/kg, preferably about 0.03 mg/kg to about 30 mg/kg.

Pharmaceutically acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include oils such as corn oil, buffers such as PBS, saline, polyethylene glycol, glycerin, polypropylene glycol, dimethylsulfoxide, an amide such as dimethylacetamide, a protein such as albumin, a detergent, such as Tween 80, mono-, oligoor polysaccharides, such as glucose, lactose, cyclodextrins and starch.

The pharmaceutical compositions may contain other active ingredients, such as antimicrobial agents and other adjuvants such as benzyl alcohol and phenol compounds and diluents conventionally used in the art.

These pharmaceutical compositions may take the form of a solution, emulsion, suspension, lotion, ointment, cream, granule, powder, tablet, capsule, sachet, lozenge, ampoule, pessary, or suppository. They may be administered parenterally, intramuscularly, subcutaneously, intravenously, intraarticularly, transdermally, orally, or buccally, as a suppository or pessary, topically, as an aerosol, spray, or drops, depending upon whether the preparation is used to treat internal or external retroviral infections.

The compounds may also be administered with other antiviral and/or biological response modifiers. For example, the compounds used in the present invention may be administered with known HIV-RT inhibitors such as ddC, AZT, and ddI or non-nucleoside RT inhibitors such as TIBO derivatives and tricyclic diazepinones, or other inhibitors which act against other HIV proteins such as protease, integrase and RNAase, as well as with biological modifiers such as alfa-, beta- or gamma- interferon or a combination thereof, interleukin-2 and GM-CSF. The dosage of ddC and AZT used in AIDS or ARC human patient has been published.

When given in combination therapy, the other anti-HIV compounds may be given at the same time as a compound used in the present invention or the dosing may be staggered as desired. The two (or more) drugs may also be combined in a composition. Doses of each drug may be less when used in combination than when they are used as a single agent.

Preferred compounds employed in the method of this invention are shown below.

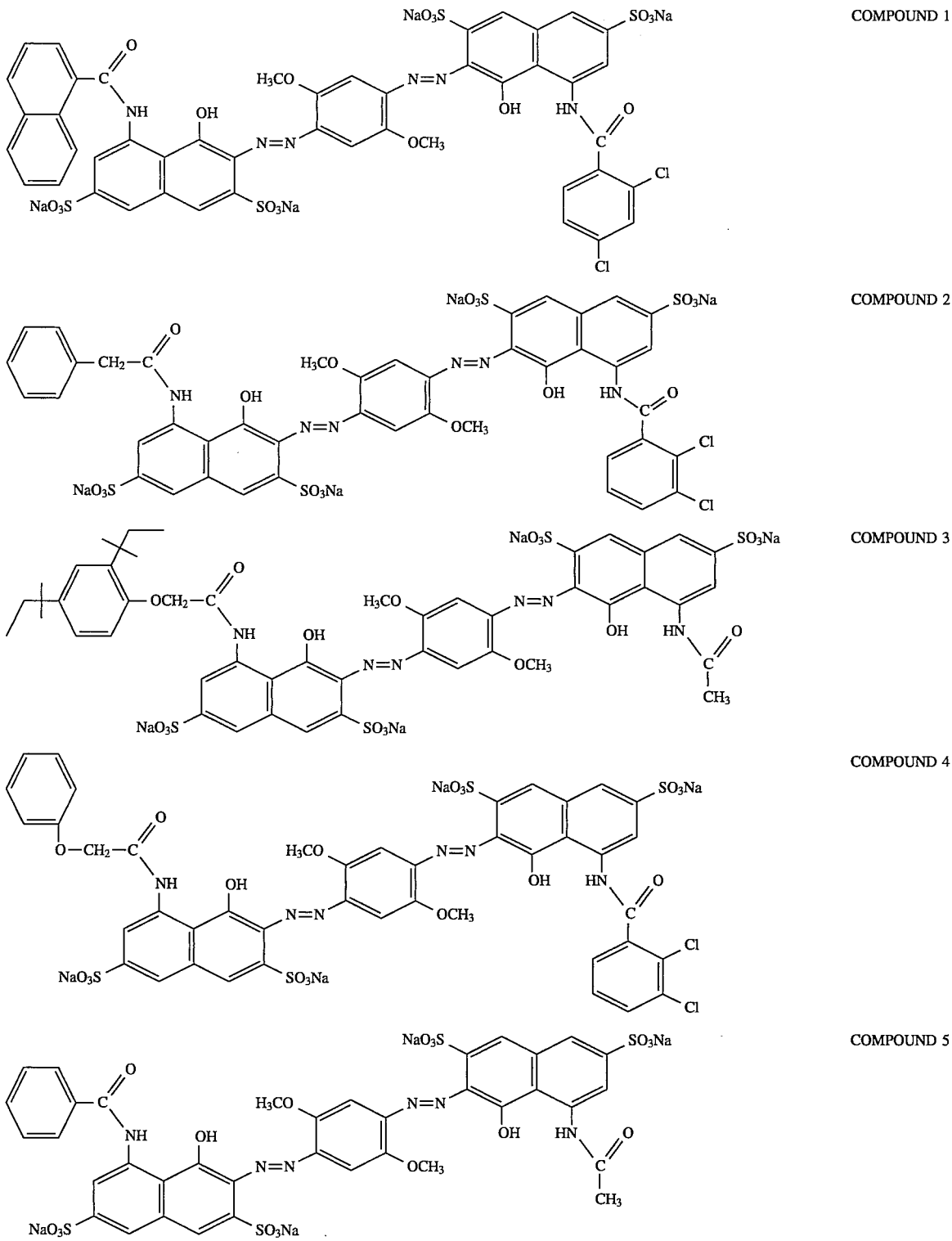

-continued
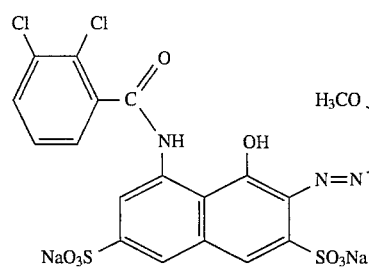 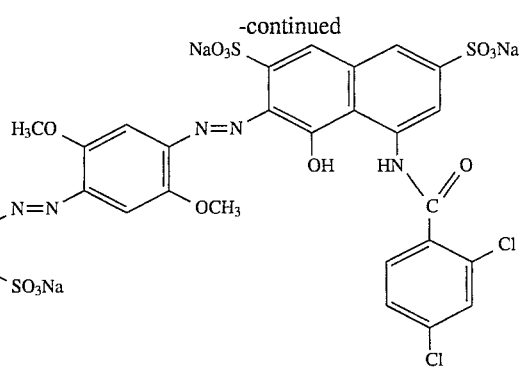
COMPOUND 6
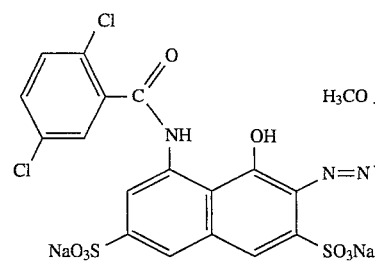 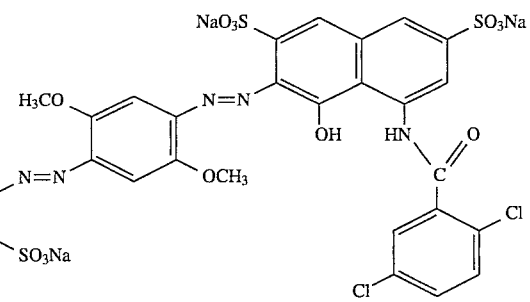
COMPOUND 7
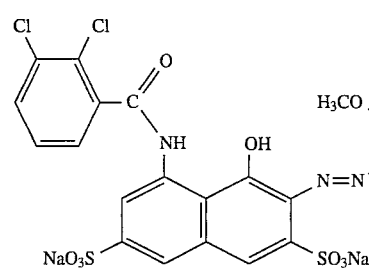 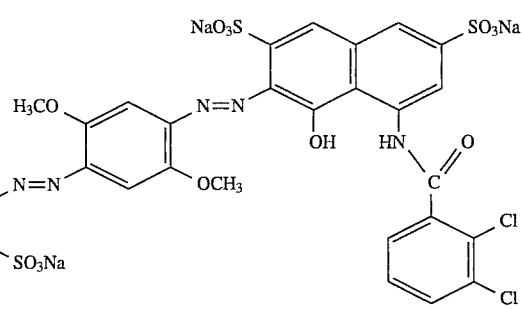
COMPOUND 8
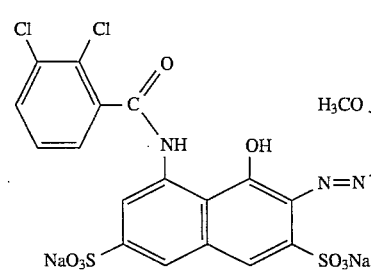 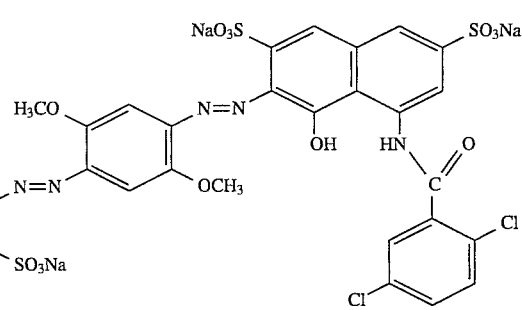
COMPOUND 9
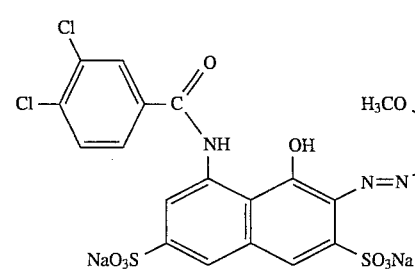 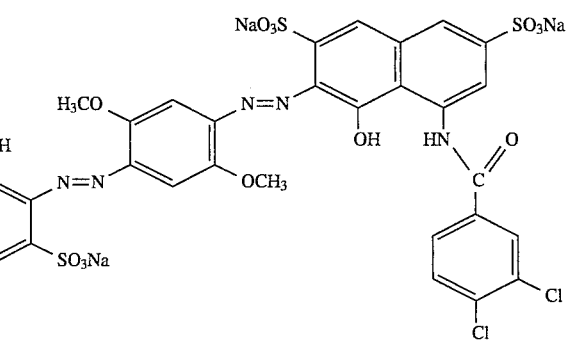
COMPOUND 10

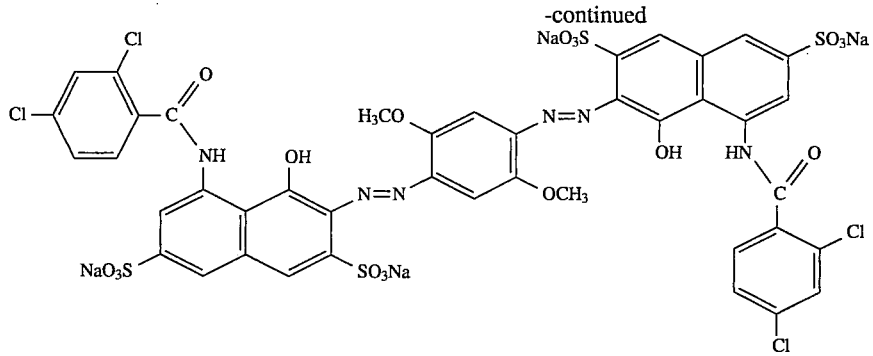
COMPOUND 11
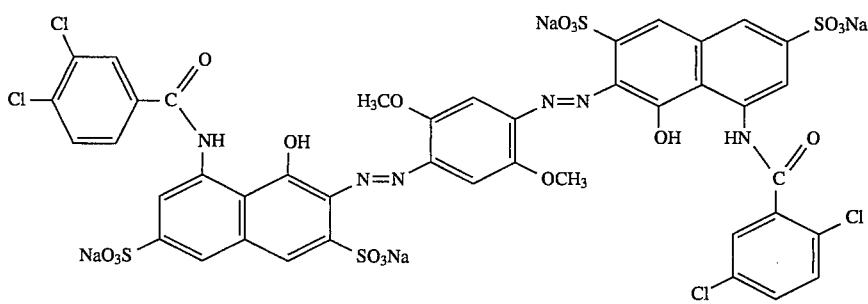
COMPOUND 12
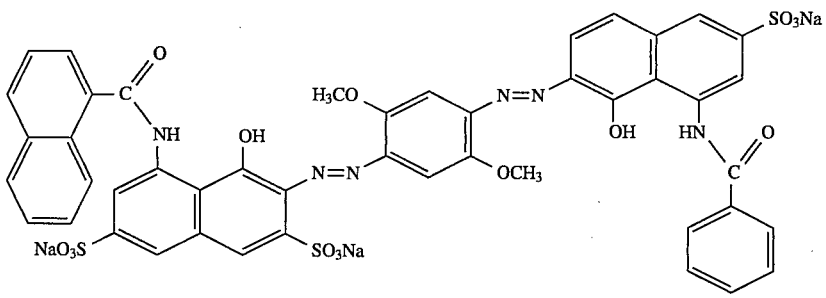
COMPOUND 13
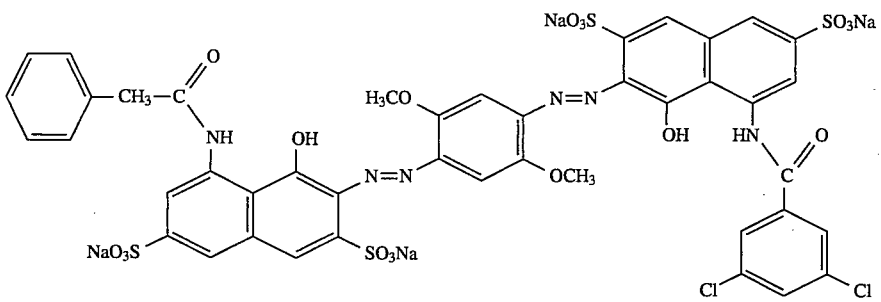
COMPOUND 14
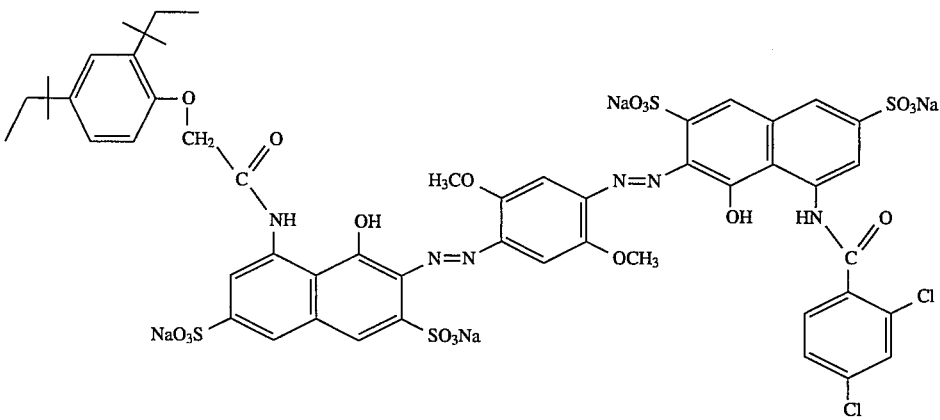
COMPOUND 15

-continued
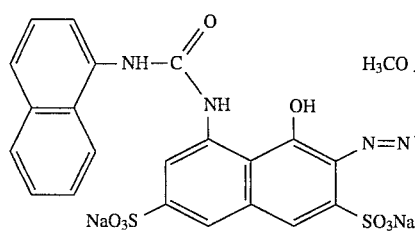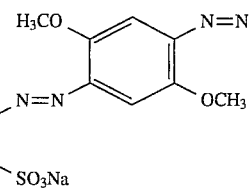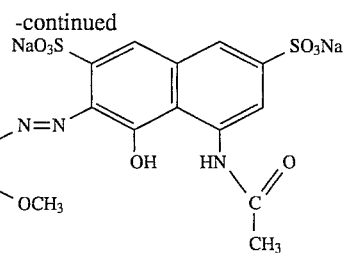
COMPOUND 16
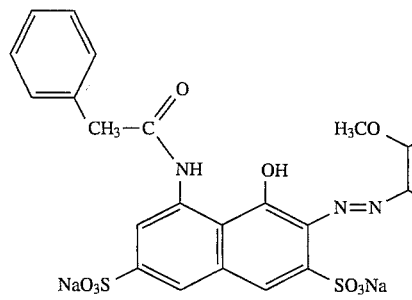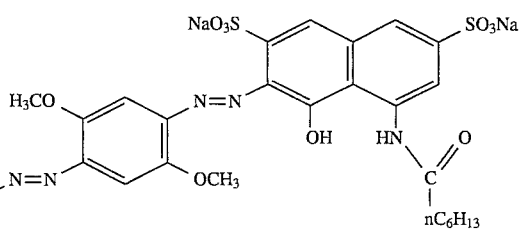
COMPOUND 17
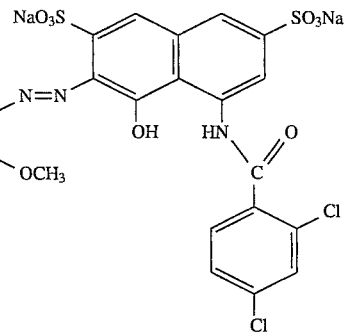
COMPOUND 18
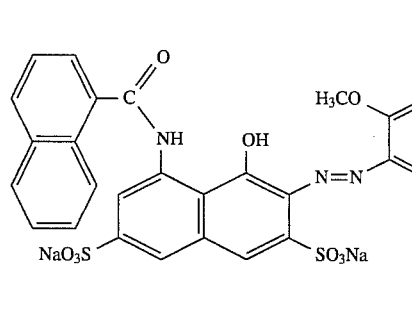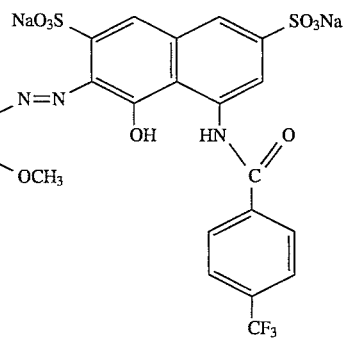
COMPOUND 19
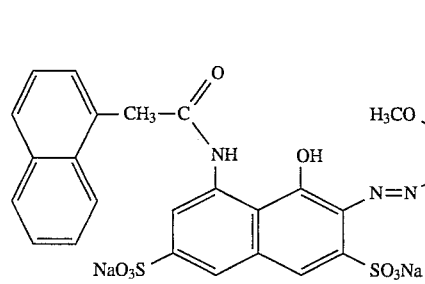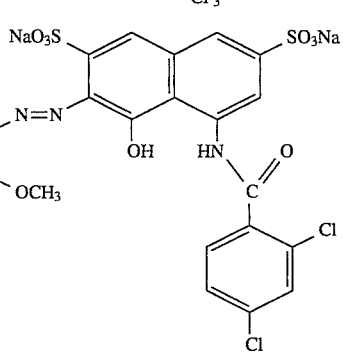
COMPOUND 20

-continued
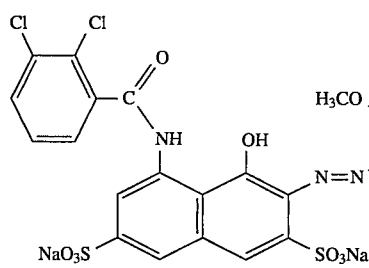 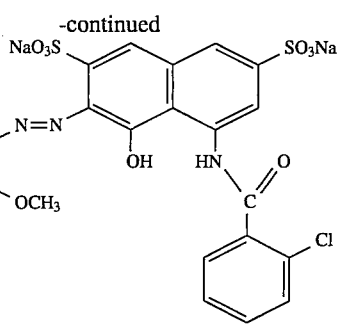
COMPOUND 21
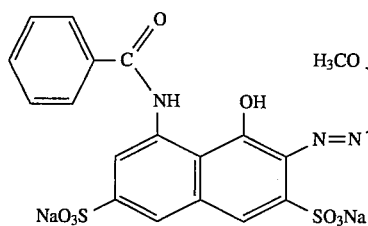 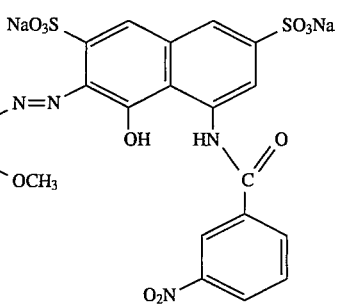
COMPOUND 22
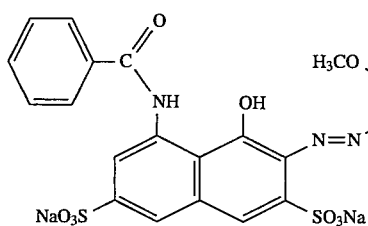 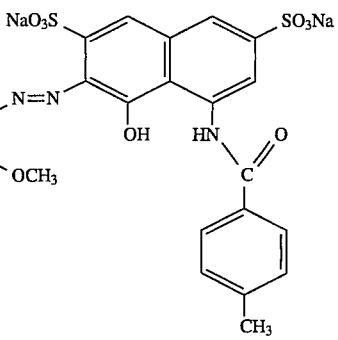
COMPOUND 23
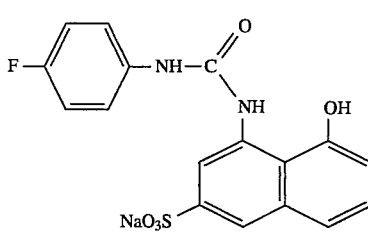 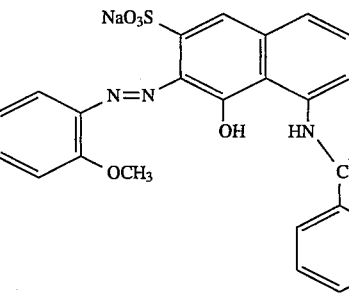
COMPOUND 24
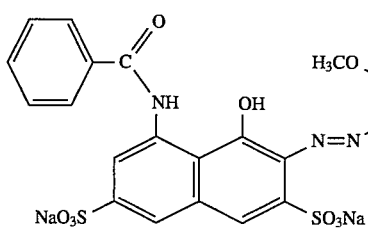 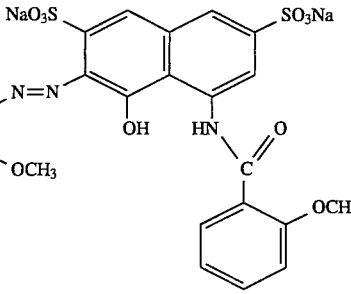
COMPOUND 25

-continued
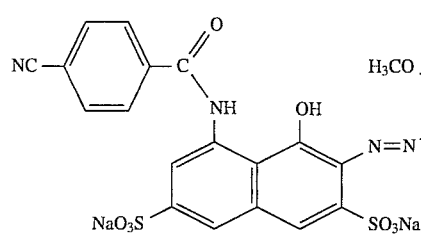 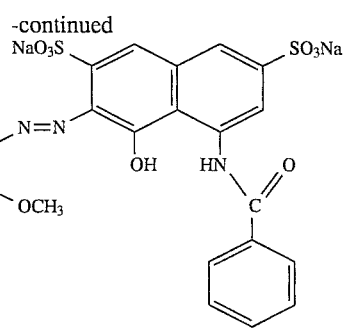
COMPOUND 26
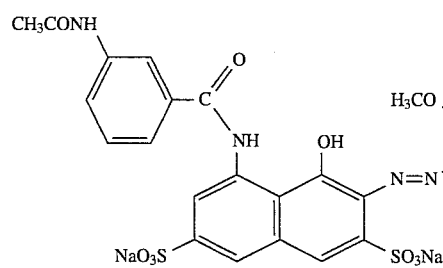 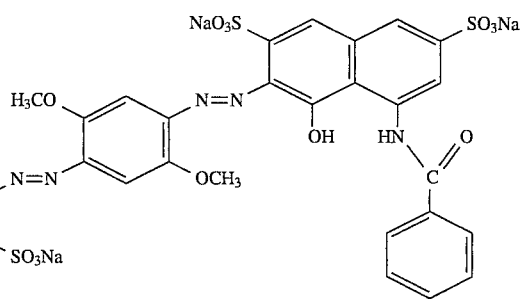
COMPOUND 27
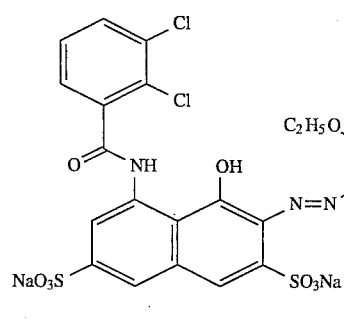 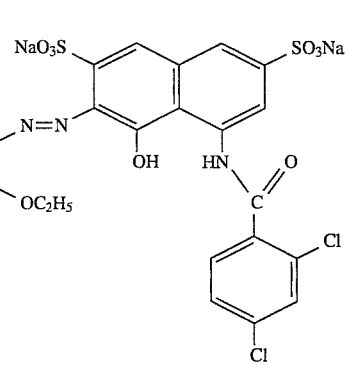
COMPOUND 28
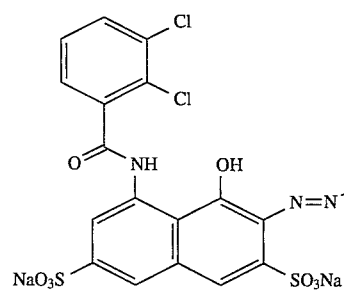 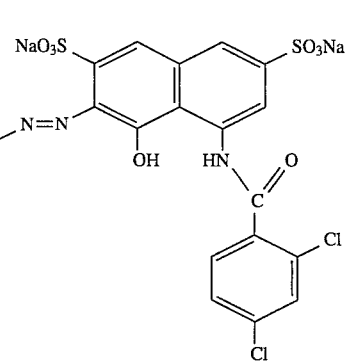
COMPOUND 29
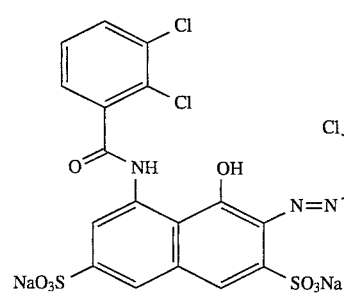 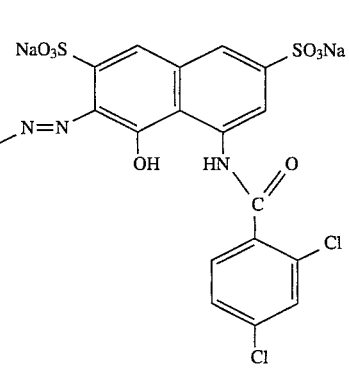
COMPOUND 30

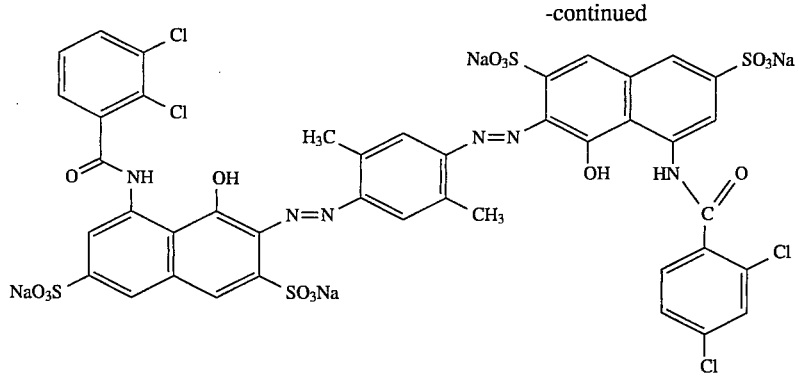
COMPOUND 31
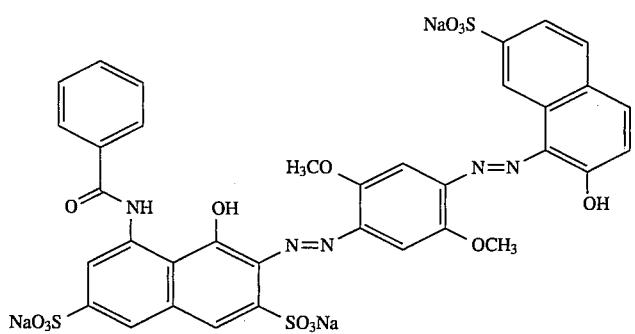
COMPOUND 32
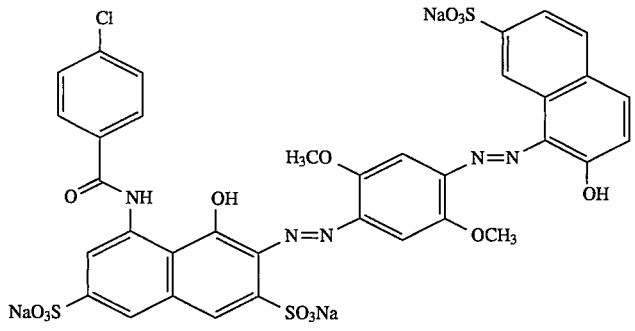
COMPOUND 33
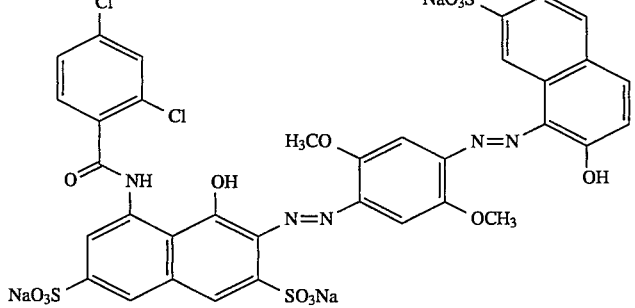
COMPOUND 34
COMPOUND 35

-continued
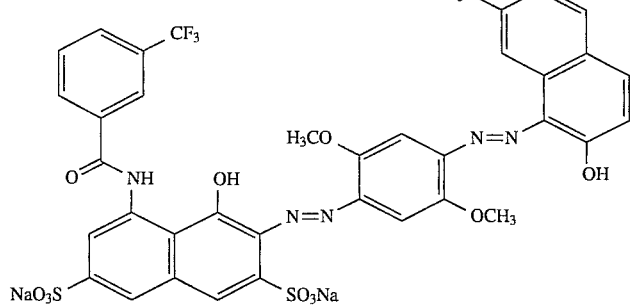
COMPOUND 36
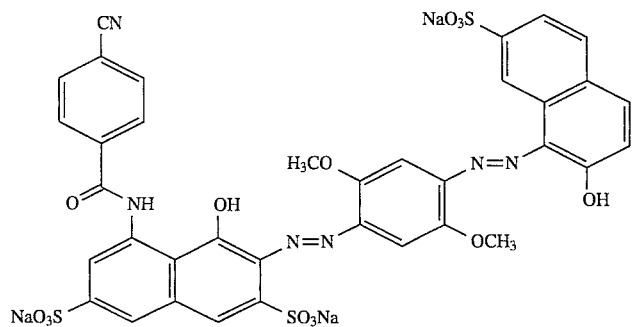
COMPOUND 37
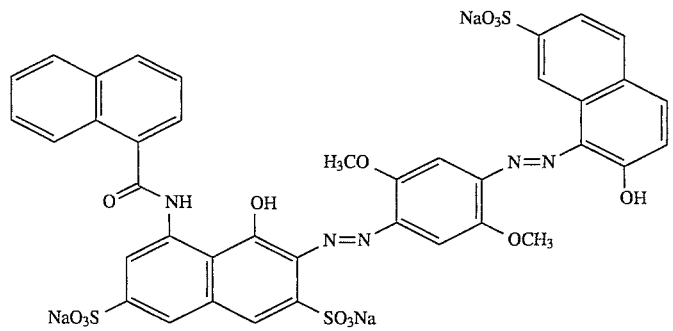
COMPOUND 38
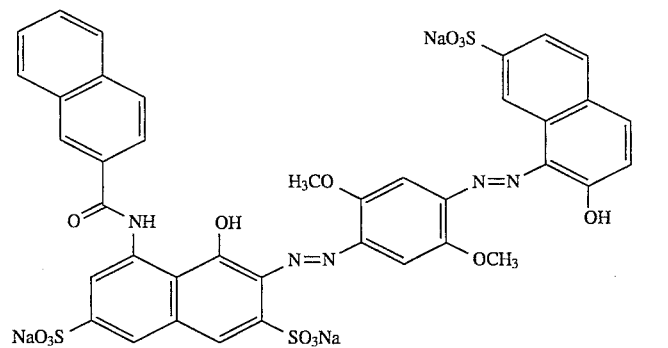
COMPOUND 39
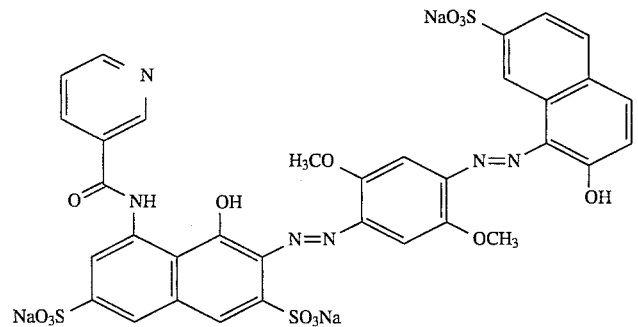
COMPOUND 40

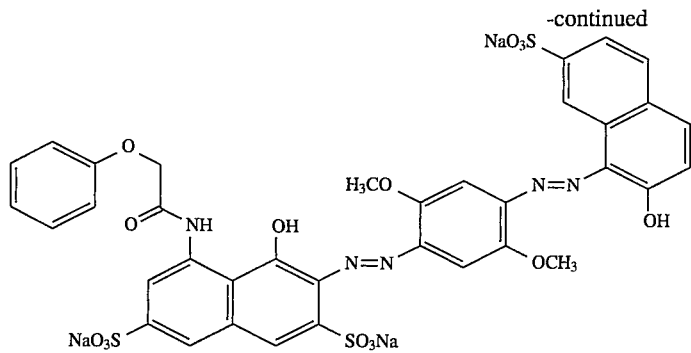
COMPOUND 41
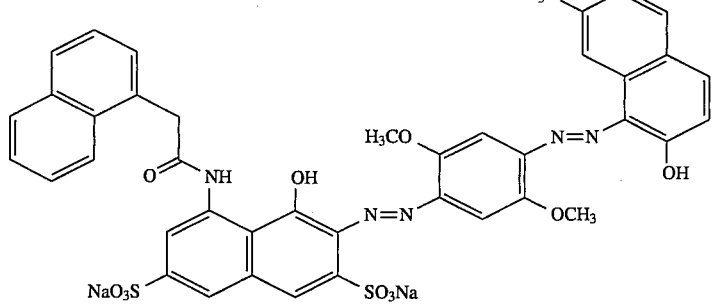
COMPOUND 42
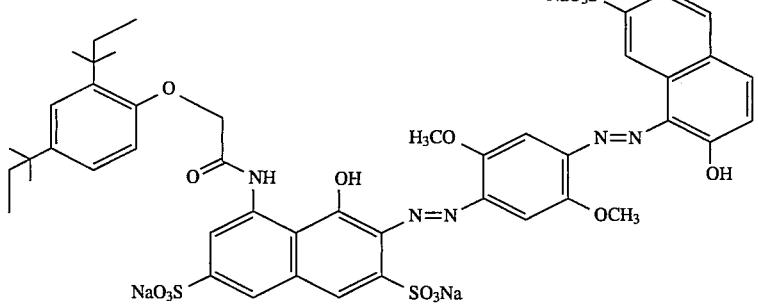
COMPOUND 43
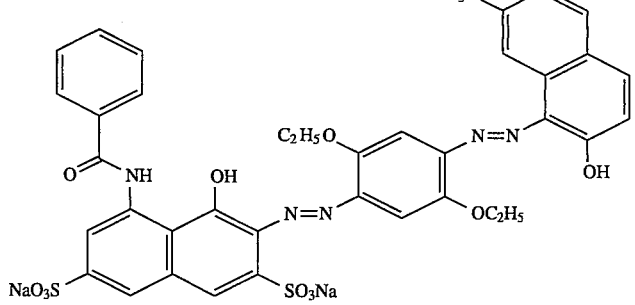
COMPOUND 44
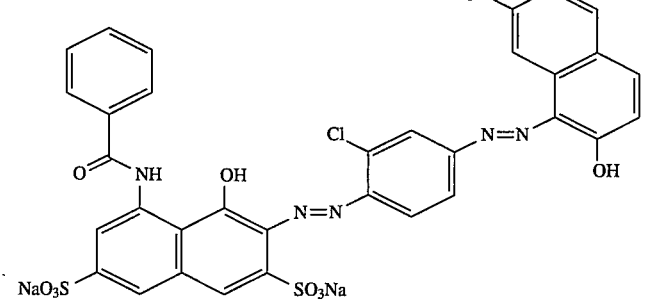
COMPOUND 45

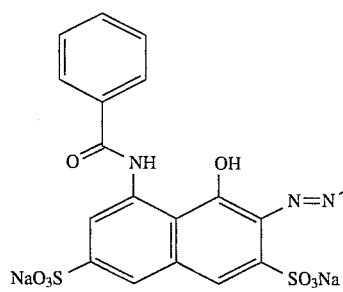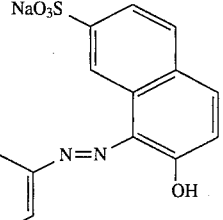
COMPOUND 46
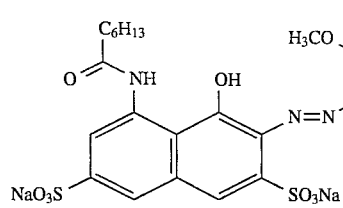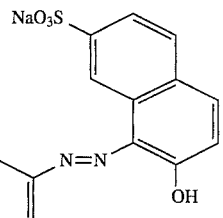
COMPOUND 47
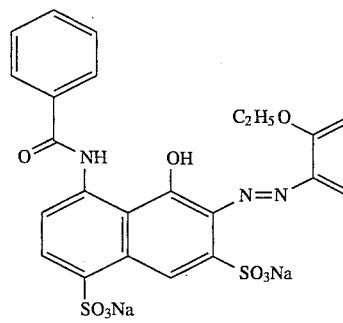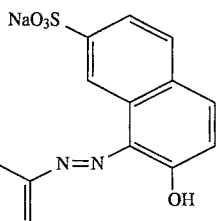
COMPOUND 48
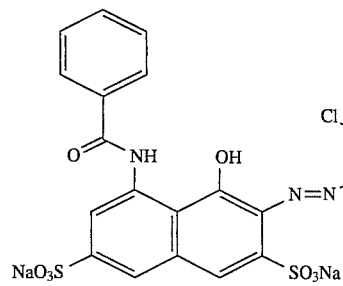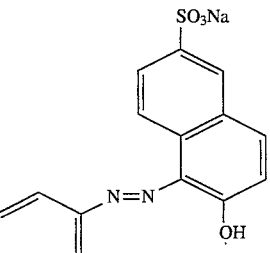
COMPOUND 49

-continued
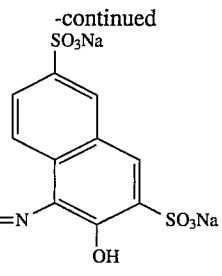
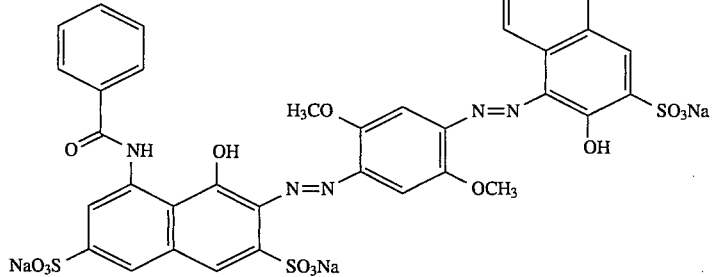
COMPOUND 50
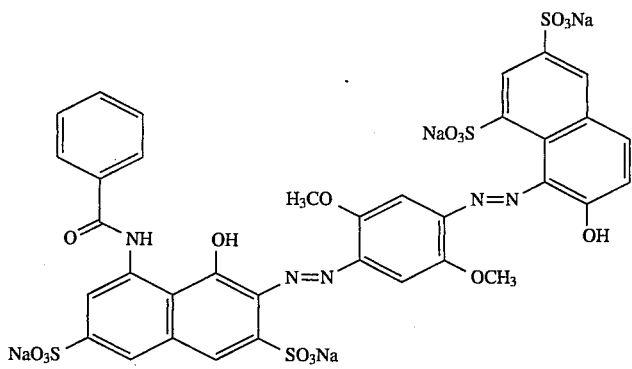
COMPOUND 51
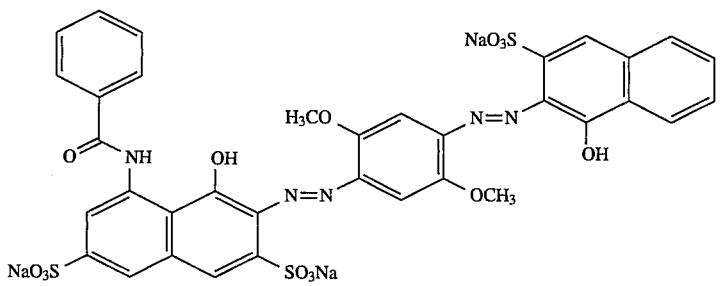
COMPOUND 52
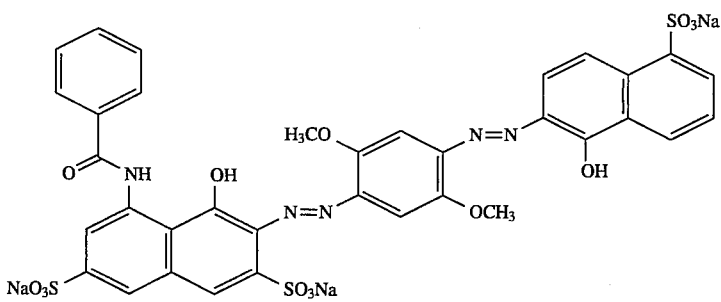
COMPOUND 53
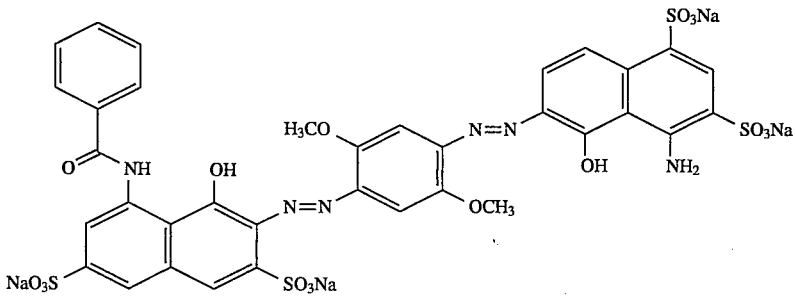
COMPOUND 54

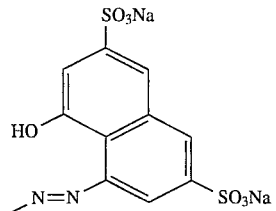
COMPOUND 55
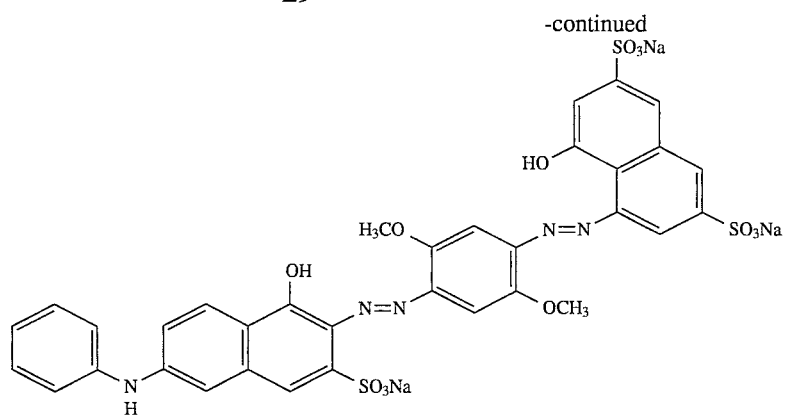
COMPOUND 56
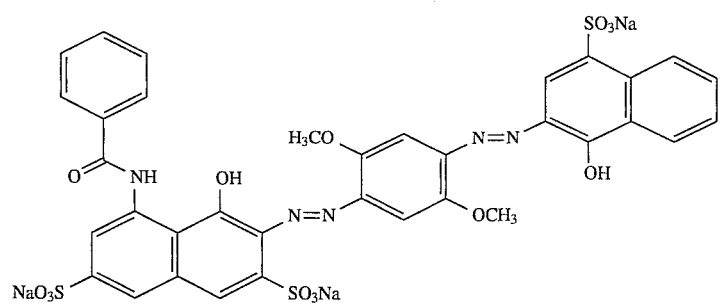
Compounds of formulas (I) to (IV) employed in the present invention are synthesized according to the method similar to that disclosed in U.S. Pat. Nos. 3,754,923 and 3,671,253, typically illustrated in a synthetic scheme of compound 6.

5,589,510
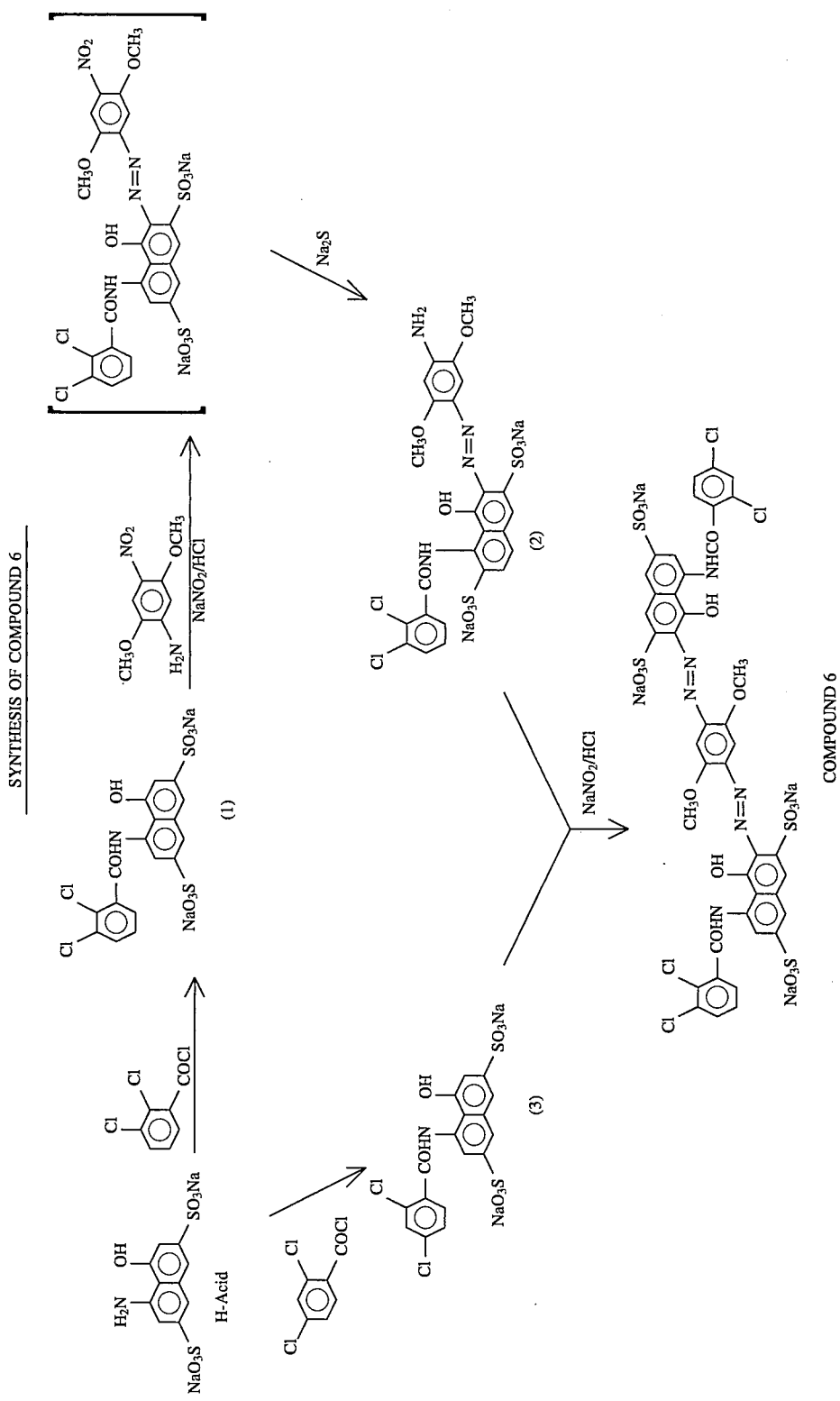

SYNTHESIS EXAMPLE

Synthesis of Compound 6
Synthesis of intermediate compound (1)

According to modified Schotten-Baumann method, intermediate compound (1) was prepared. In deionized water (200 ml), there were dissolved 8-amino-3,6-disulfo-1-naphthol (H-acid, 34.2 g, 100 mmol as monosodium salt), sodium hydroxide (5.0 g, 125 mmol) and sodium carbonate (37.0 g, 350 mmol). To the solution, a solution of 2,3-dichlorobenzoyl chloride (23.1 g, 110 mmol) in tetrahydrofuran (20 ml) was added dropwise at 35° to 40° C. over about 1 hour under a flow of nitrogen gas. The reaction mixture was vigorously stirred for 1 hour at the same temperature, then for 1 hour at 80° C. A 10% sodium chloride aqueous solution (250 ml) was added to the solution and cooled to room temperature. The precipitate was filtered, washed with a 10% sodium chloride aqueous solution followed by acetonitrile and dried giving 40.0 g of compound (1) (as disodium salt) in a 75% yield.

Synthesis of intermediate compound (3)

According to modified Schotten-Baumann method, intermediate compound (3) was prepared. In deionized water (400 ml), there were dissolved 8-amino-3,6-disulfo-1-naphthol (H-acid, 68.2 g, 200 mmol as monosodium salt), sodium hydroxide (8.6 g, 140 mmol) and sodium carbonate (12.7 g, 120 mmol). To the solution, 2,4-dichlorobenzoyl chloride (46.1 g, 220 mmol) was added dropwise at 38° to 44° C. over about 1 hour under a flow of nitrogen gas. The reaction mixture was vigorously stirred for 1 hour at the same temperature, then for 1 hour at 80° C. A 10% sodium chloride aqueous solution (80 ml) was added to the solution and cooled to 35° C. The precipitate was filtered, washed with a 10% sodium chloride aqueous solution followed by acetonitrile and dried giving 82 g of compound (3) (as disodium salt) in a 77% yield.

Synthesis of intermediate compound (2)

2,5-Dimethoxy-4-nitroaniline (4 g, 20 mmol) was dissolved in deionized water (20 ml) containing conc. HCl (5.1 ml). To the solution, a solution of sodium nitrite (1.56 g, 22 mmol) in deionized water (10 ml) was added under ice cooling. The reaction mixture was stirred at the same temperature for 60 minutes. The diazonium salt aqueous solution thus prepared was added at 10° C. to a solution of the compound (1) (12 g, 22.2 mmol as disodium salt) and sodium acetate (5.5 g) in deionized water (200 ml). The resultant mixture was stirred at 20° C. for 1 hour and then for 1 hour at 45° C.

To the reaction mixture, there was added a 20% sodium hydroxide solution (9 ml) followed by the addition of sodium sulfide nona-hydrate (19.2 g, 80 mmol). The mixture was stirred for 1 hour at 45° C. Isopropyl alcohol (50 ml) was added to the reaction mixture. Then acetic acid (9 ml) and saturated sodium acetate aqueous solution (30 ml) were added successively to neutralize the solution. The precipitate was filtered and washed with a mixed solvent of a 10% sodium acetate aqueous solution and isopropyl alcohol (1:1 by volume) and then isopropyl alcohol.

The crude product (intermediate compound (2)) was suspended in a mixed solvent of toluene (160 ml) and isopropyl alcohol (40 ml) and vigorously stirred under reflux condition. The precipitate was filtered, washed with a mixed solvent of toluene and isopropyl alcohol (4:1 by volume), and dried giving 12.2 g of the intermediate compound (2) (as disodium salt) in an 84% yield.

Synthesis of Compound 6

To a solution of the intermediate compound (2) (10 g, 14 mmol) in deionized water (120 ml), conc. HCl (3.5 ml) was added under ice cooling and vigorously stirred. To the solution, a solution of sodium nitrite (1.18 g, 17 mmol) in deionized water (10 ml) was added and stirred for 60 minutes under ice cooling to prepare a diazonium salt.

The intermediate compound (3) (9 g, 16.8 mmol) was dissolved in deionized water (60 ml). To the solution, pyridine (30 ml) was added followed by the addition of the suspension of the diazonium salt at 10° to 15° C. The reaction mixture was stirred at room temperature for 60 minutes and then for 30 minutes at 50° C. The reaction mixture was heated to 70° C. to which isopropyl alcohol (200 ml) and saturated sodium acetate aqueous solution (60 ml) were added and then cooled to 50° C. The precipitate was filtered, washed with a 10% sodium acetate aqueous solution, then a mixed solvent of isopropyl alcohol and water (4:1 by volume) followed by isopropyl alcohol, and dried.

The crude product (Compound 6) was dissolved in water (150 ml) at 80° C., to which isopropyl alcohol (600 ml) was added dropwise at 70° C. The reaction mixture was cooled to 50° C. The precipitate was filtered and washed with a mixed solvent of isopropyl alcohol and water (4:1 by volume) followed by isopropyl alcohol, and dried giving 9.5 g of Compound 6 (7.5 mmol) in a 54% yield. Decomposition point: 282° C.; λ max: 717 nm (DMSO; ε=87,700 $M^{-1}$ $cm^{-1}$).

It should also be noted that the compounds of the present invention cause tautomerism such as, for example, between a keto form and a hydrazo form as shown below:

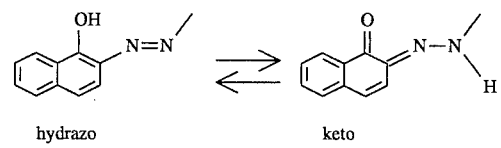

hydrazo      keto

An example of such tautomerism is shown below with respect to Compound 6:

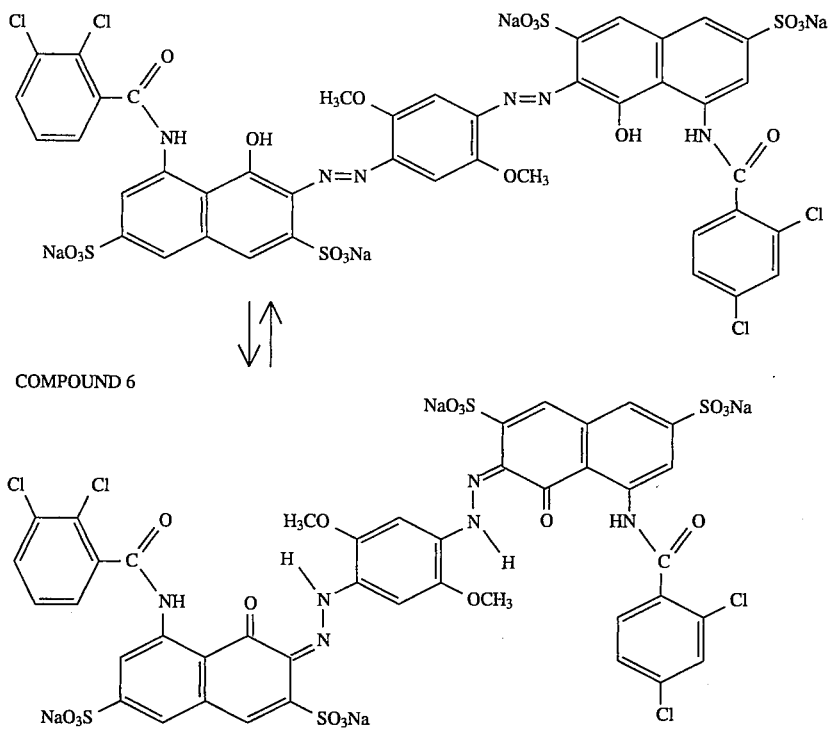

COMPOUND 6

PREPARATION EXAMPLE (Preparation of intravenous injection (freeze-dried vial))

Compound 6 (1 g) and D-glucose (1 g) were dissolved in water for injection (100 ml) and stirred at room temperature for one hour and at 80° C. for 20 minutes. The solution was sterilized by filtration through a 0.22 μm membrane filter. Two ml of the sterilized solution was placed in an endotoxin-free vial (30 ml). The vial was freeze-dried by liquid nitrogen at −90° C. for 24 hours and sealed with a rubber cap under reduced pressure.

Example 1

(Syncytia Assay)

A cell culture based syncytia assay was used for the rapid and quantitative detection of compounds that can prevent fusion between virus, and/or virus infected cells with cells expressing CD4, a glycoprotein of 55 kDa on the surface of the cells. As discussed above, it is believed that the main route for HIV infection into lymphocytes and macrophages is through CD4 (Fauci, Science, 239:617 (1988); Stein et al., Cell, 49:659 (1987); McClure et al., EMBO J., 7:521 (1988); and Maddon et al., Cell, 54:865 (1986)). CD4 interacts with the membrane expressed gp120 on HIV-1 and HIV-1-infected cells (Dalgleish et al., Nature, 312:763 (1984); Klatzmann et al., Nature, 312:767 (1984); McDougal et al., Science, 231:382 (1986); and Maddon et al., Cell, 47:333 (1986)). This CD4-gp120 interaction is essential for syncytia formation, a process of cell fusion that leads to giant cell aggregates and eventually the in vitro destruction of virus-infected cells (Lifson et al., Nature, 323:725 (1986); and Sodroski et al., Nature, 322:470 (1986)). Some have speculated that the process of syncytia formation recruits uninfected CD4 cells, and may be a factor in the decreased $CD4^+$ cell counts in HIV-1 infected individuals. However, the exact mechanism and cell components involved with syncytia formation after the initial gp120-CD4 binding are still unknown. An ELISA containing just the gp120 and CD4 proteins alone is unable to provide additional components thought to be important in HIV-1 infectivity and cell fusion, such as conformational changes of the proteins, newly exposed gp41 sites and other as yet unknown sites on the cell (Sattentau et al., J. Exp. Med., 174:407 (1991); and Gallaher, Cell, 50:327 (1987)). Therefore, the in vitro assay described below can be used to assess not only gp120-CD4 binding, but all the necessary events needed for syncytia formation.

The gp160-expressing cell line, Chinese Hamster Ovary (CHO) cell line (Urlaub et al., Proc. Natl. Acad. Sci. USA, ZZ; 4216 (1980)) that had been genetically altered to express the HIV envelope protein, gp160, was used in the assay. This genetic alternative was achieved using an expression vector, containing cDNA encoding gp160 and also DNA encoding dihydrofolate reductase (DHFR). The CHO cell line is deficient in dihydrofolate reductase. Therefore, the clones that survive when grown in methotrexate express gp160. Once expressed, gp160 is cleaved into gp41, a membrane bound form and gp120 which is non-covalently attached to gp41. These cells are grown in 12.5 μM methotrexate, 10% (v/v) fetal calf serum in alpha MEM media supplemented with 100 units/ml penicillin, 100 μg/ml of streptomycin and 2 mM of L-glutamine.

The human T Cell line SupT (Smith et al, Cancer Research, 44; 5657 (1984)) was used as the $CD4^+$ cell line in this assay. SupT cells are grown in RPMI, supplemented with 10% (v/v) fetal calf serum, 100 unit/ml penicillin, 100 μg/ml streptomycin and 2 mM L-glutamine. A stock solution of the test compound used in this invention in 100% DMSO was diluted into RPMI media. Next, $4.0 \times 10^4$ gp160 expressing CHO cells were mixed with $2 \times 10^5$ SupT cells into 200 μl of RPMI media in a 96-well cell culture plate, in the presence or absence of 5μg/ml of the test compound. The 96-well plate was placed into a $CO_2$ incubator at 37° C. overnight. The syncytia were microscopically counted using phase contrast optics. Each test compound was tested in triplicate for statistical significance. The results obtained are shown in Table 1 below.

TABLE 1

SYNCYTIA INHIBITION ASSAY
Inhibition (%)

| Compound | Inhibition (%) 5 µg/ml | Inhibition (%) 1 µg/ml |
|---|---|---|
| 1 | 100 | 53 |
| 5 | 82 | 9 |
| 6 | 100 | 33 |
| 7 | 88 | 37 |
| 8 | 73 | 37 |
| 9 | 91 | 17 |
| 10 | 99 | 39 |
| 12 | 98 | 69 |
| 13 | 86 | 20 |
| 14 | 23 | 6 |
| 15 | 99 | 48 |
| 16 | 100 | 44 |
| 18 | 85 | 34 |
| 19 | 100 | 25 |
| 20 | 99 | 82 |
| 28 | 100 | 57 |
| 30 | 74 | 46 |
| 31 | 93 | 35 |
| 34 | 100 | 70 |
| 36 | 80 | N.D. |
| 38 | 100 | 60 |
| 39 | 74 | 45 |
| 42 | 98 | 11 |
| 43 | 100 | 81 |
| 44 | 100 | 19 |
| 45 | 100 | 30 |
| 49 | 96 | 39 |
| 50 | 100 | 83 |
| 53 | 97 | 55 |
| 54 | 94 | 55 |
| 56 | 100 | 16 |
| CSB | 100 | 67 |

CSB = Chicago Sky Blue
In the presence of 10% fetal calf serum (FCS)

Most of the anti-syncytia assay data of the compounds used in this invention correlates with antiviral data. Although each absolute inhibition value is different between the two, the higher the anti-syncytia value, the higher the antiviral activity. Since gp120/CD4 blocking activity does not correlate with the antiviral activity, this type of compound used in this invention likely blocks a step of the fusion process that occurs after CD4 binding.

Example 2

(Mutagenicity)

It is well known that several dyes with anti-HIV activity which have a bis-azo biphenyl struture, e,g., EB and CSB, exhibit strong mutagenic effects in the standard Ames Test (K-T. Chung et al, Mutation Research, 277, 201–220 (1992)) because of the formation of mutagenic benzidine molecules in vivo.

On the other hand, the compounds employed in the present invention do not have any such moiety. As shown in Table 2 below, most of the compounds used in the present invention gave negative values or very low positive values of mutagenicity in the Ames Test.

The results obtained are shown in Table 2 below. Six *Salmonella typhimuriumstrai* strains, TA98, TA1535, TA1537, TA1538, TA100 and W2P2uvr were used in this experiment.

TABLE 2

Ames Test (in the presence of S9)

| Compound | Result | $LD_{50}$ |
|---|---|---|
| 1 | Negative | 150 mg/kg |
| 2 | Negative | 150 |
| 3 | Negative | 150 |
| 4 | Negative | 160 |
| 5 | Negative | 120 |
| 6 | Negative | 130 |
| 7 | Positive (0.05 colony no/g g) | 170 |
| 8 | Negative | 160 |
| 9 | Negative | 150 |
| 10 | Negative | 140 |
| 11 | Positive (0.02 colony no/µg) | 160 |
| 12 | Negative | 190 |
| 13 | Negative | 160 |
| 14 | Positive (0.12 colony no/µg) | 160 |
| 15 | Negative | 150 |
| 16 | Positive (0.03 colony no/µg) | 160 |
| 17 | Negative | 130 |
| 18 | Negative | 135 |
| 19 | Negative | 140 |
| 20 | Positive (0.08 colony no/µg) | 150 |
| 21 | Negative | 160 |
| 22 | Positive (0.4 colony no/µg) | 140 |
| 23 | Negative | 130 |
| 24 | Negative | 140 |
| 25 | Negative | 160 |
| 26 | Negative | 150 |
| 28 | Negative | |
| 29 | Negative | |
| 30 | Negative | |
| 31 | Negative | |
| 34 | Negative | |
| 36 | Negative | |
| 37 | Negative | |
| 38 | Negative | |
| 39 | Negative | |
| 40 | Negative | |
| 41 | Negative | |
| 42 | Negative | |
| 43 | Negative | |
| EB*1 | Positive (10 colony no/µg) | 100 |
| CBS*2 | Positive (10 colony no/µg) | 100 |

*1 Evans Blue;
*2 Chicago Sky Blue
Note: This unit is described in the literature and represents specific activity. The higher the value, the higher the mutagenicity.

Most of the examples of compounds used in this invention showed negative or very weak positive values. Although a direct comparison of each absolute value cannot be made with those in the literature because the absolute value will change depending on the experimental conditions as well as the activity of the liver homogenate (S9) used. When compared with EB and CSB under this condition, it is very clear that the compounds used in this invention have very low mutagenic potential.

Example 3

(Reverse Transcriptase Inhibition Assay)

Inhibition of recombinant reverse transcriptase (RT) was performed by using commercially available Boehringer Mannheim RT assay kit (Cat. No. 1468 120) based on incorporation of digoxigenin labeled dUTP into DNA. Recombinant enzyme from HIV-1 was purchased from Worthington Biochemical Corporation. The level of anti-RT activity in the sample was determined by measurement of absorbance using an ELISA reader at 405 nm.

The results obtained are shown in Table 3 below.

TABLE 3

| Compound | Inhibition (%) at 0.5 μM) | Inhibition (%) (at 5.0 μM) |
|---|---|---|
| 1 | 70 | — |
| 3 | 77 | — |
| 6 | 32 | 80 |
| 7 | 41 | 75 |
| 10 | 55 | — |
| 11 | 30 | — |
| 16 | — | 98 |
| 18 | — | 66 |
| Evans Blue | 48 | — |
| Suramin | 68 | — |

— = ND

The compounds used in this invention show an inhibitory effect against reverse transcriptase like CSB and Suramin. Again, since this activity does not always correlate with antiviral activity, the antiviral activity can not be explained only by this RT activity.

Example 4

(LD50 Values)

The test material was administered intravenously to 5 female mice in five increasing doses. Mortalities were recorded within 1 week, and the LD50 was determined with the aid of statistical calculations. The LD50 values are shown in Table 2 above.

As shown in Table 2, LD50 values for the compounds used in the present invention were found to be very high, more than 130 mg/kg in the case of all Compounds 1 to 26. When one compares these results to Evans Blue (100 mg/kg), Suramin (40 mg/kg), and Fuchsin Acid (100 mg/kg), it is apparent that the compounds of the present invention also have an advantage in terms of lower toxicity.

Example 5

(Antiviral Assay)

HIV-1 infectivity studies were conducted in CEM, H9, MT2 cells and peripheral blood mononuclear cells (PBMC). CEM, H9 and MT2 were grown in RPMI1640 medium, 10% heat-inactivated fetal bovine serum (FBS). PBMCs were stimulated with 4 μg/ml PHA for 48 hours in RPMI1640, 10% FBS before HIV-1 infection. After HIV-1 infection, PBMCs were maintained in RPMI 1640, 10% FBS and 10 10 units/ml IL-2. The major HIV-1 isolates used were MN, IIIB, SF2, AZT-sensitive A018 and AZT-resistant A018 provided by NIH AIDS research and reference reagent program. Two major antiviral assays were developed to determine the antiviral activities of the compounds of this invention (as inhibitors).

Experimental Protocols

I. The cells were infected with HIV-1 RF or IIIB at an infectivity multiplicity (moi) of 0.001 in the absence of a compound of this invention for one hour. HIV-1 infected cells were washed once with PBS, resuspended in RPMI1640, 10% FBS medium and distributed in 24-well culture dishes (5×10$^5$ cells per well) in the presence of a compound of this invention as inhibitor. The cell culture was maintained for seven days and the virus spread was assessed by HIV-1 p24 ELISA.

II. The HIV-1 viruses were incubated with a compound of this invention for one hour in 24 well-culture dishes before cells were added (5×10$^5$ cells/well). The moi was 0.001. Compounds and cell-free viruses were washed out after overnight incubation. The cell culture with fresh RPMI1640, 10% FBS was maintained for 7 days and the virus production was assessed by HIV-1 p24 ELISA.

The cytotoxity was assessed using MTS assays (R. J. Gulakowski et al., J. of Virological Methods, 33, 87(1991)).

The results obtained with HIV-1 RF are shown in Table 4 below.

TABLE 4

Inhibitory Effects of Naphthalenesulfonic Acid Compounds (NSA)

| Experimental Protocol* | Compound | Condition No.** | Concentration (μg/ml) | | | | |
|---|---|---|---|---|---|---|---|
| | | | 5 | 2.5 | 1.25 | 0.6 | 0.3 |
| | | | % Inhibition (after day 10) | | | | |
| I | 1 | A | 100 | 100 | 100 | 98 | — |
| I | 2 | A | 98 | 73 | 60 | — | — |
| I | 3 | A | 100 | 100 | 96 | — | — |
| I | 5 | A | 100 | 100 | 87 | 45 | — |
| I | 6 | A | 100 | 100 | 100 | 100 | 99 |
| I | 6 | B | 100 | 99 | 64 | 63 | — |
| I | 7 | A | 100 | 100 | 99 | 81 | — |
| I | 7 | B | 97 | 48 | 0 | 0 | — |
| I | 8 | A | 99 | 99 | 99 | 87 | — |
| I | 8 | B | 95 | 0 | 0 | — | — |
| I | 9 | A | 100 | 99 | 99 | 63 | — |
| I | 9 | B | 90 | 16 | 0 | 0 | — |
| I | 11 | A | 100 | 100 | 100 | 100 | 99 |
| I | 11 | B | 98 | 93 | 87 | 55 | — |
| I | 12 | A | 100 | 100 | 99 | 96 | 86 |
| I | 12 | B | 93 | 40 | 0 | 0 | — |
| II | 14 | A | 98 | 56 | 50 | — | — |
| II | 15 | A | 100 | 89 | 61 | — | — |
| II | 17 | A | 100 | 98 | 72 | — | — |
| I | 28 | A | 100 | 100 | 100 | — | — |
| I | 31 | A | 100 | 88 | 0 | — | — |
| I | 38 | A | 100 | 99 | 99 | — | — |
| I | 42 | A | 99 | 99 | 28 | — | — |
| I | 43 | A | 99 | 0 | 0 | — | — |
| I | 45 | A | 99 | 99 | 92 | — | — |
| I | Suramin | A | 0 | 0 | 0 | — | — |
| I | CSB | A | — | 90 | 70 | 37 | — |

*Experimental Protocol I, II: see the experimental protocol description above.
**Conditions:
A: In the presence of 10% FCS
B: In the presence of 50% Human Serum The results in Table 4 indicate that the compounds used in the present invention exhibit an efficient inhibitory effect against HIV even in the presence of 50% Human Serum.

Example 6

The inhibitory effects of additional naphthalenesulfonic acid compounds were tested as follows: Experimental Details:

PBMCs were activated for 48 hours in conditioned medium containing PHA at a concentration of 4 μg/ml. Thereafter 10$^6$ cells were plated in each of the 24 well plates containing 10% FCS or 50% FCS. The test compound, previously dissolved in a glucose solution (1 mg/ml), was then added to each of the wells to achieve the appropriate concentration. The plate was then incubated overnight (about 15 hours) after which 50 μl of cell-free HIV-1 patient isolate was added to each well. The plates were incubated for further 6 to 8 hours after which all free floating solution of virus was washed off. Washing was performed four times.

After removal of the virus, all cultures were resuspended in conditioned medium containing 10% FCS.

For control experiments virus growth was monitored in either 10% FCS or 50% FCS throughout the observation period (15 days).

For glucose placebo experiments, similar amounts of glucose by volume were added to each of the wells in either 10% or 50% FCS wells as that required for the compounds being tested.

TABLE 5

Inhibitory Effects of Naphthalenesulfonic Acid Compounds (NSA)

| Patient Isolate | Cell Type | Compound | Condition No.* | \multicolumn{5}{c}{Concentration (μg/ml)} |
| | | | | 20 | 10 | 5 | 2.5 | 1.0 |
| | | | | \multicolumn{5}{c}{% Inhibition (after day 12)} |
|---|---|---|---|---|---|---|---|---|
| IH | PBMCs | 6 | A | 100 | 82 | 91 | 0 | — |
| IH | PBMCs | 6 | B | 100 | 90 | 80 | 13 | — |
| IH | PBMCs | 21 | A | 100 | 77 | 23 | 0 | — |
| IH | PBMCs | 21 | B | 100 | 61 | 23 | 10 | — |
| IH | PBMCs | 11 | A | 100 | 100 | 0 | 0 | — |
| IH | PBMCs | 11 | B | 100 | 31 | 0 | 0 | — |
| IH | PBMCs | 12 | A | 100 | 100 | 85 | 0 | — |
| IH | PBMCs | 12 | B | 93 | 90 | 0 | 0 | — |
| IH | CD4+ | 1 | A | 100 | 50 | — | — | — |
| IH | PBMCs | 5 | A | 77 | 77 | 45 | — | — |
| IH | PBMCS | 13 | A | 100 | 70 | 55 | — | — |
| IH | PBMCs | 4 | A | 98 | 88 | 60 | — | — |
| NIH 900285 | PBMCs | 6 | A | — | — | 99 | 95 | 0 |
| NIH 900285 | PBMCs | 28 | A | — | — | 98 | 67 | 0 |

*Conditions:
A: In the presence of 10% FCS
B: In the presence of 50% Human Serum The results in Table 5 indicate the inhibitory effect of several described compounds against HIV patient isolates.

Example 7

Animal Model Protocol

Immunodeficient CB-17 SCID (severe combined immunodeficient) mice were reconstituted with human peripheral blood cells (Scid-hu). Two weeks after engraftment, the presence of human IgG indicating the presence of functional T and B cells was confirmed. Four weeks after engraftment, SCID-hu mice were infected with $10^6$ tissue culture infectious doses/ml (TCID) of RF strain by ip injection.

This dose of virus has previously been shown to result in infection of 100% of SCID hu mice in several weeks. Twenty-four hours after infection, 8 infected mice were treated daily with Compound 6 aqueous 5% glucose solution by ip injection at a dose of 50 mg/kg for only five days. The same dose of D-(+)-glucose was injected into SCID hu mice as a control. One month after final ip dose, peritoneal cells from the mice were cocultured with human lymphocytes. After four weeks, cultures were scored for the production of virus by assaying HIV-1 p24 levels in the supernatant. As shown in Table 6, none of the 8 mice receiving Compound 6 had any detectable HIV specific p24 above the background of the no virus control. On the other hand, 5 of the 8 control mice had cultivated virus. These results demonstrate that treatment for 5 days with Compound 6 was sufficient to prevent infection of reconstituted human immune cells in an animal model.

TABLE 6

SCID Mouse Model

| Sample | P24(pg/ml) Day 28 |
|---|---|
| Virus (−) | 91.24 |
| Virus (+) | 2330 |
| Compound 6 | 46.36 |
| Compound 6 | 35.44 |
| Compound 6 | 32.61 |
| Compound 6 | 40.90 |
| Compound 6 | 34.41 |
| Compound 6 | 34.36 |
| Compound 6 | 49.46 |
| Compound 6 | 58.02 |
| Control | 1862 |
| Control | 33.92 |
| Control | 34.60 |
| Control | 7941 |
| Control | 33.97 |
| Control | 11193 |
| Control | 5580 |
| Control | 2145 |

While the invention has been described in detail, and with reference to specific embodiments thereof, it will be apparent to one of ordinary skill in the art that various changes and modifications can be made therein without departing from the spirit and scope thereof.

What is claimed is:

1. A method for treating retroviral infection in a subject comprising administering to said subject a therapeutically effective amount of a naphthalenesulfonic acid compound of formula (I) or a pharmaceutically acceptable salt thereof:

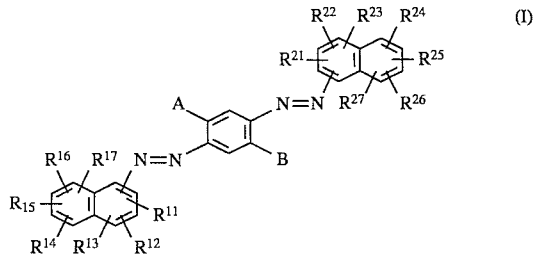

wherein $R^{11}$ to $R^{27}$ are individually selected from the group consisting of a hydrogen atom, a hydroxyl group, an amino group which is optionally substituted with an alkyl group or an aryl group, a sulfo group, a carboxyl group, an amide group which is optionally substituted with an alkyl group or an aryl group, an acylamino group, a sulfonamide group, a sulfonylamino group, an alkoxy group and a halogen atom;

provided that at least one of $R^{11}$ to $R^{17}$ is a hydroxyl group or an amino group, at least one of $R^{21}$ to $R^{27}$ is a hydroxyl group or an amino group, at least one of $R^{11}$ to $R^{17}$ is a sulfo group, and at least one of $R^{21}$ to $R^{27}$ is a sulfo group;

A and B are individually selected from the group consisting of a hydrogen atom, an alkyl ($C_1$–$C_4$) group, an alkoxy ($C_1$–$C_4$) group, and a halogen atom.

2. The method of claim 1, wherein the method comprises administering the naphthalenesulfonic acid of formula (I) or a pharmaceutically acceptable salt thereof with a pharmaceutically acceptable carrier selected from the group consisting of an oil, a buffer, saline, a polyethylene glycol, an amino acid, a detergent, an absorption enhancer, a lipid, dimethylsulfoxide, a protein, a monosaccharide, an oligosaccharide and a polysaccharide.

3. The method of claim 2, wherein said pharmaceutically acceptable carrier is selected from the group consisting of an oil, a protein, an amino acid, a detergent, a lipid, a polyethylene glycol, a monosaccharide, an oligosaccharide and a polysaccharide.

4. A method for treating a retroviral infection in a subject comprising administering to said subject a therapeutically effective amount of a naphthalenesulfonic acid compound or a pharmaceutically acceptable salt thereof which is selected from the group consisting of the following compounds;

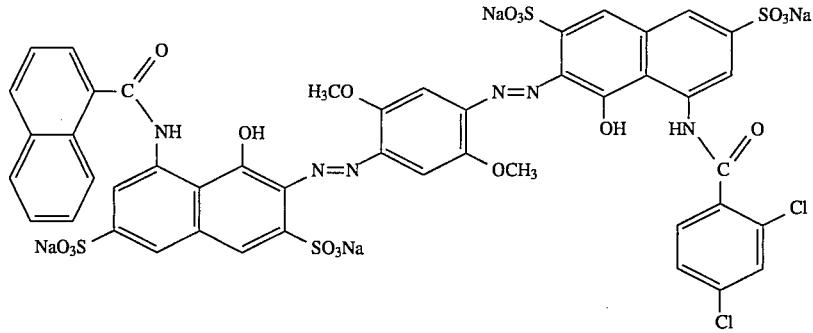

COMPOUND 1

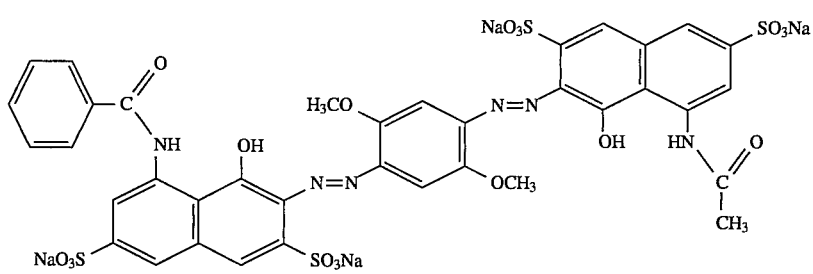

COMPOUND 5

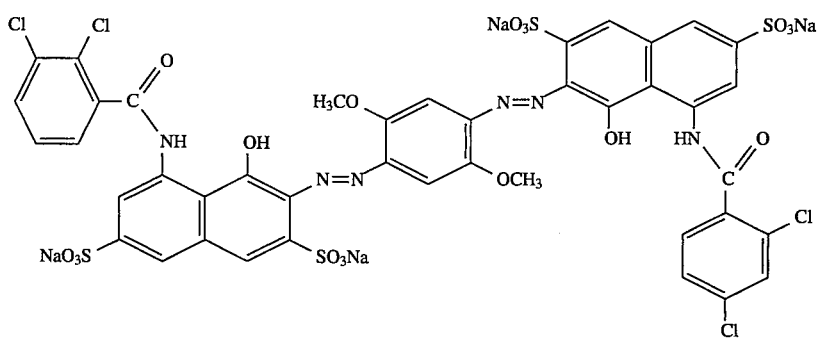

COMPOUND 6

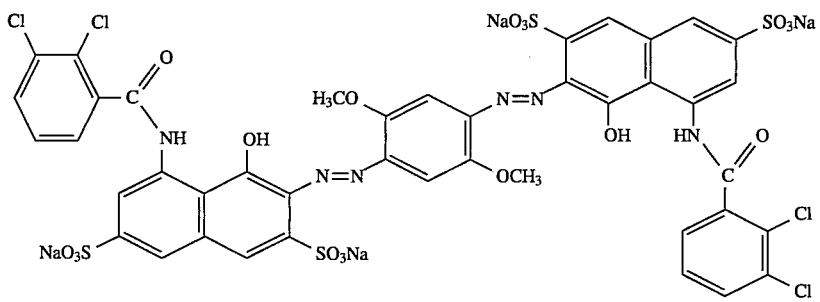

COMPOUND 8

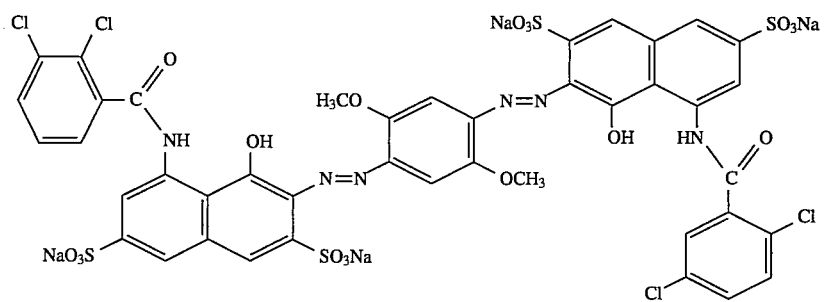

COMPOUND 9

-continued

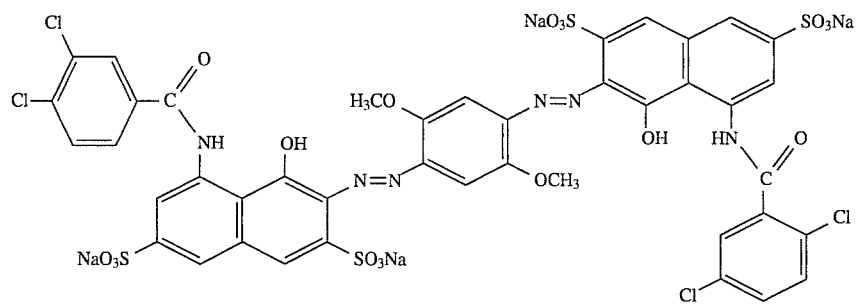

COMPOUND 12

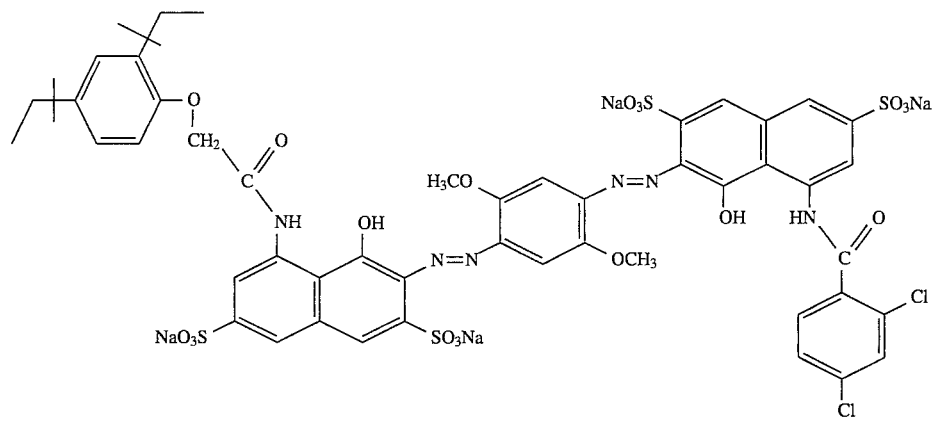

COMPOUND 15

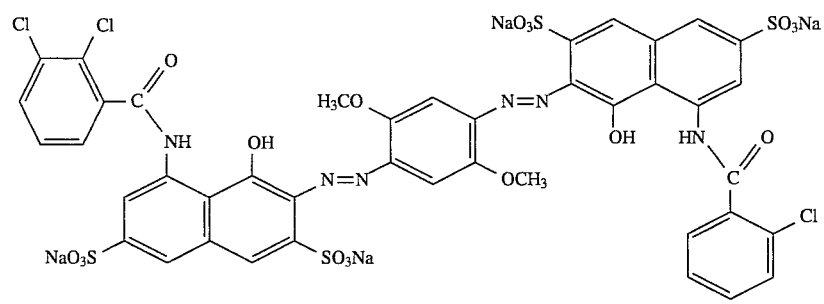

COMPOUND 21 and

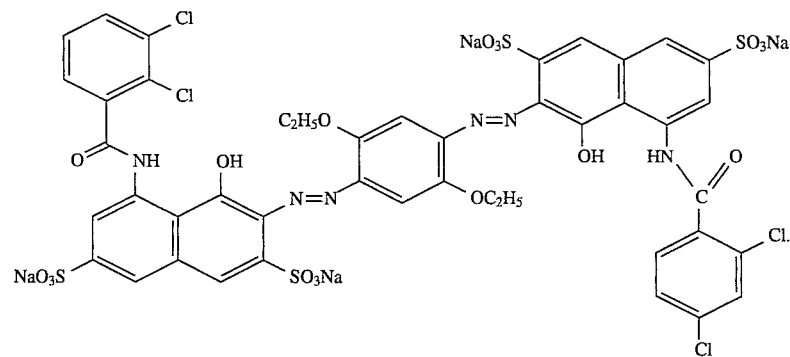

COMPOUND 28

5. The method of claim 1, wherein the method comprises administering the naphthalenesulfonic acid of formula (I) or a pharmaceutically acceptable salt thereof orally, topically or by injection.

6. The method of claim 1, wherein said method comprises administering said naphthalenesulfonic acid compound of formula (I) or a pharmaceutically acceptable salt thereof in the form of a controlled release formulation.

7. The method of claim 1, wherein said method comprises administering said naphthalenesulfonic acid compound of formula (I) or a pharmaceutically acceptable salt thereof in the form of a biodegradable implant.

8. A method for treating a retroviral infection in a subject comprising administering to said subject a therapeutically effective amount of a naphthalenesulfonic acid compound represented by formula (II) or a pharmaceutically acceptable salt thereof:

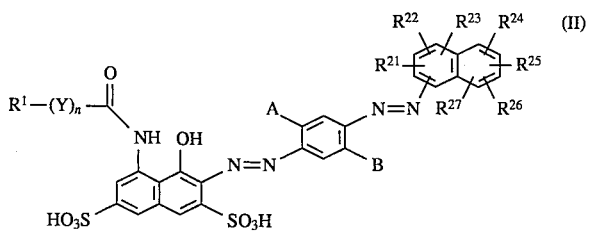

wherein $R^{21}$ to $R^{27}$ are individually selected from the group consisting of a hydrogen atom, a hydroxyl group, an amino group which is optionally substituted with an alkyl group or an aryl group, a sulfo group, a carboxyl group, an amide group which is optionally substituted with an alkyl group or an aryl group, an acylamino group, a sulfonamide group, a sulfonylamino group, an alkoxy group and a halogen atom;

provided that at least one of $R^{21}$ to $R^{27}$ is a hydroxyl group or an amino group, and at least one of $R^{21}$ to $R^{27}$ is a sulfo group;

A and B are individually selected from the group consisting of a hydrogen atom, an alkyl ($C_1$–$C_4$) group, an alkoxy ($C_1$–$C_4$) group, and a halogen atom;

$R^1$ is selected from the group consisting of a substituted or unsubstituted alkyl ($C_1$–$C_{12}$) group, a substituted or unsubstituted aryl ($C_6$–$C_{12}$) group, and a substituted or unsubstituted heteroaryl ($C_1$–$C_{12}$) group, Y represents —NH—, —$CH_2$—, or —$OCH_2$—; and n is 0 or 1.

9. A method for treating a retroviral infection in a subject comprising administering to said subject a therapeutically effective amount of a naphthalenesulfonic acid compound represented by formula (III) or a pharmaceutically acceptable salt thereof:

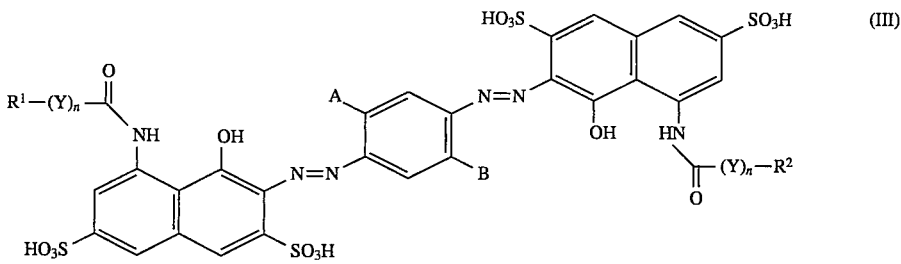

wherein $R^1$ and $R^2$ are individually selected from the group consisting of a substituted or unsubstituted alkyl ($C_1$–$C_{12}$) group, a substituted or unsubstituted aryl ($C_6$–$C_{12}$) group, and a substituted or unsubstituted heteroaryl ($C_1$–$C_{12}$) group;

A and B are individually selected from the group consisting of a hydrogen atom, an alkyl ($C_1$–$C_4$) group, an alkoxy ($C_1$–$C_4$) group, and a halogen atom;

Y represents —NH—, —$CH_2$—, or —$OCH_2$—; and n is 0 or 1.

10. The method of claim 9, wherein the method comprises administering the naphthalenesulfonic acid of formula (III) or a pharmaceutically acceptable salt thereof with a pharmaceutically acceptable carrier selected from the group consisting of an oil, a buffer, saline, a polyethylene glycol, an amino acid, a detergent, an absorption enhancer, a lipid, dimethylsulfoxide, a protein, a monosaccharide, an oligosaccharide and a polysaccharide.

11. The method of claim 10, wherein said pharmaceutically acceptable carrier is selected from the group consisting of an oil, a protein, an amino acid, a detergent, a lipid, a polyethylene glycol, a monosaccharide, an oligosaccharide and a polysaccharide.

12. The method of claim 9, wherein the method comprises administering the naphthalenesulfonic acid of formula (III) or a pharmaceutically acceptable salt thereof orally, topically or by injection.

13. The method of claim 9, wherein said method comprises administering said naphthalenesulfonic acid compound of formula (III) or a pharmaceutically acceptable salt thereof in the form of a controlled release formulation.

14. The method of claim 9, wherein said method comprises administering said naphthalenesulfonic acid compound of formula (III) or a pharmaceutically acceptable salt thereof in the form of a biodegradable implant.

* * * * *